United States Patent
Hoshino et al.

(10) Patent No.: US 7,288,395 B2
(45) Date of Patent: Oct. 30, 2007

(54) ACC GENE

(75) Inventors: Tatsuo Hoshino, Kanagawa-ken (JP); Kazuyuki Ojima, Kanagawa-ken (JP); Yutaka Setoguchi, Kanagawa-ken (JP)

(73) Assignee: DSM IP Assets B.V., TE Heerlen (NL)

( * ) Notice: Subject to any disclaimer, the term of this patent is extended or adjusted under 35 U.S.C. 154(b) by 0 days.

(21) Appl. No.: 10/528,847

(22) PCT Filed: Sep. 25, 2003

(86) PCT No.: PCT/EP03/10683

§ 371 (c)(1),
(2), (4) Date: Feb. 10, 2006

(87) PCT Pub. No.: WO2004/029232

PCT Pub. Date: Apr. 8, 2004

(65) Prior Publication Data

US 2006/0172372 A1    Aug. 3, 2006

(30) Foreign Application Priority Data

Sep. 27, 2002 (EP) .................................. 02021625

(51) Int. Cl.
*C12Q 1/68* (2006.01)
*C12P 21/06* (2006.01)
*C12N 1/21* (2006.01)
*C12N 1/19* (2006.01)
*C12N 9/10* (2006.01)
*C12N 15/70* (2006.01)
*C07H 21/04* (2006.01)

(52) U.S. Cl. ................. 435/183; 435/69.1; 435/252.33; 435/254.21; 435/67; 435/193; 435/320.1; 435/471; 536/23.2

(58) Field of Classification Search ................ 435/193, 435/67, 252.3, 69.1, 471; 536/23.2
See application file for complete search history.

(56) References Cited

FOREIGN PATENT DOCUMENTS

| EP | 1 035 206 A1 | 9/2000 |
|---|---|---|
| EP | 1 158 051 A1 | 11/2001 |
| WO | WO 99/32635 | 7/1999 |
| WO | WO 00/11199 | 3/2000 |

*Primary Examiner*—Rebecca E. Prouty
*Assistant Examiner*—Iqbal Chowdhury
(74) *Attorney, Agent, or Firm*—Bryan Cave LLP

(57) ABSTRACT

The present invention relates to a gene useful in a process to increase the microbial production of carotenoids. The carotenoids astaxanthin is distributed in a wide variety of organisms such as animals, algae and microorganisms. It has a strong antioxidation property against reactive oxygen species. Astaxanthin is used as a coloring reagent, especially in the industry of farmed fish, such as salmon, because astaxanthin imparts distinctive orange-red coloration to the animals and contributes to consumer appeal in the marketplace.

16 Claims, 2 Drawing Sheets

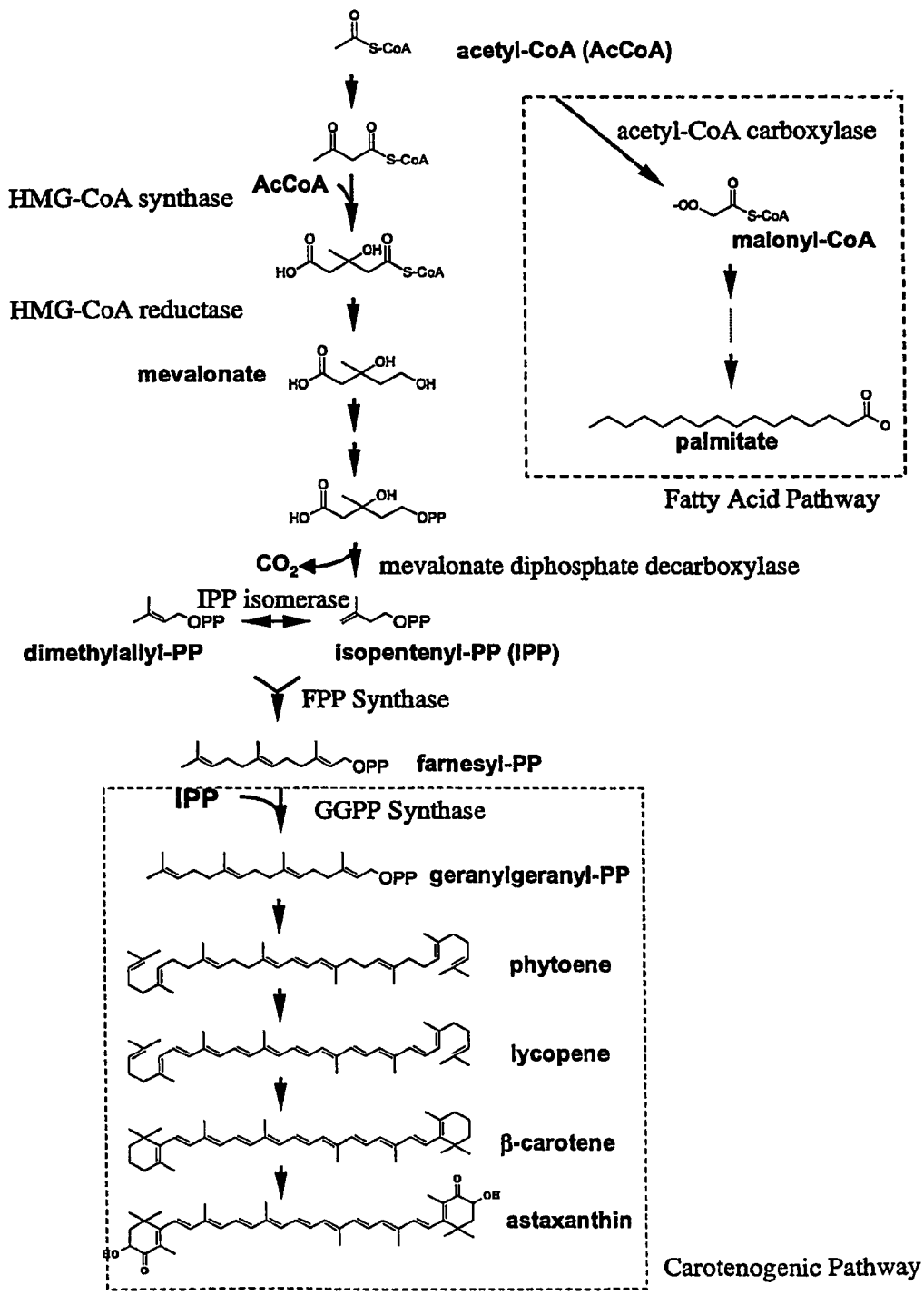
FIG.1 Biosynthetic pathway of astaxanthin and fatty acid in *Phaffia rhodozyma*

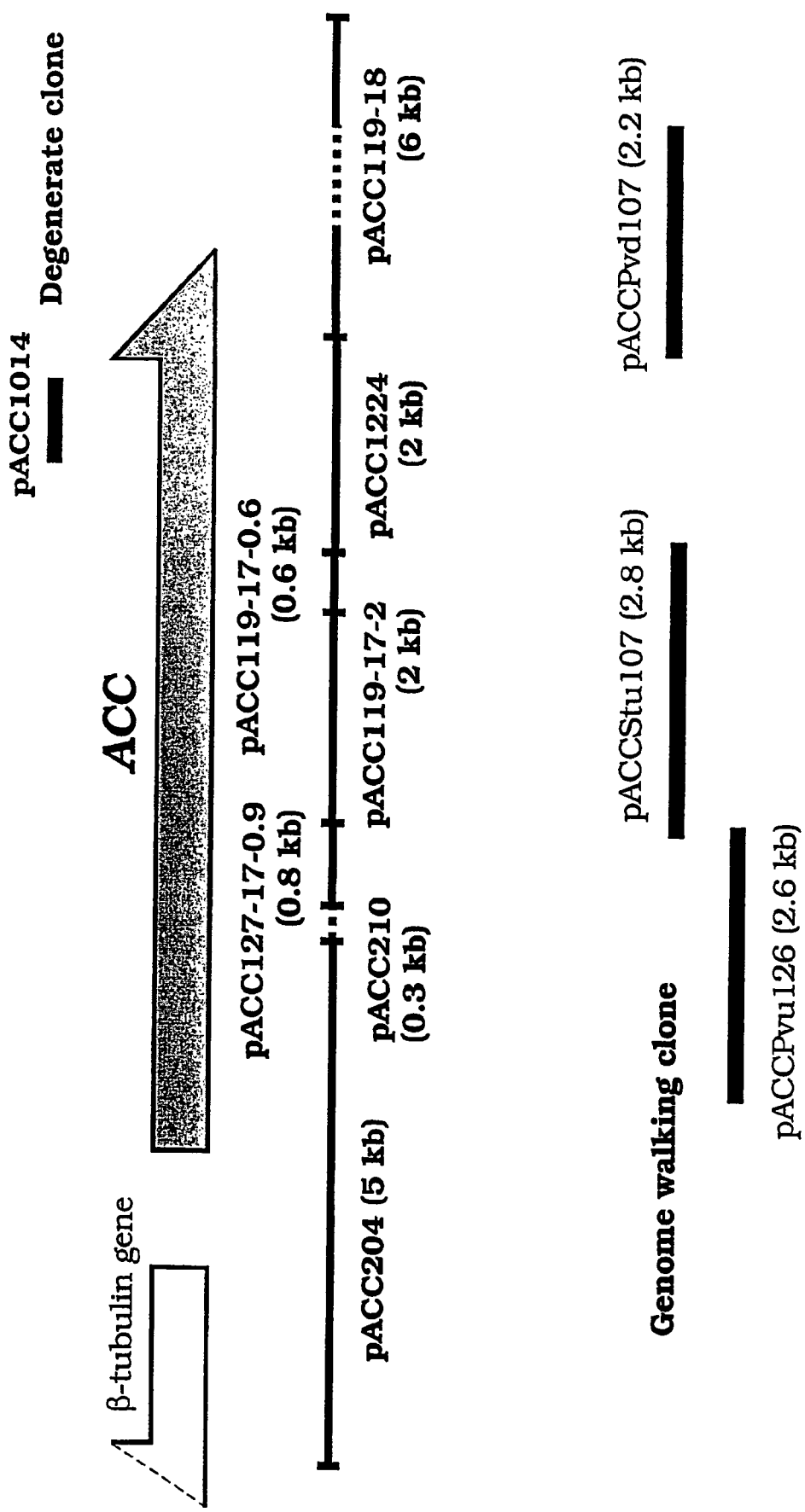
FIG.2 Cloning of ACC gene region from *P. rhodozyma*

ACC GENE

This application is the National Stage of International Application No. PCT/EP2003/010683, filed Sep. 25, 2003.

The present invention relates to a gene useful in a process to increase the microbial production of carotenoids.

The carotenoid astaxanthin is distributed in a wide variety of organisms such as animals, algae and microorganisms. It has a strong antioxidation property against reactive oxygen species. Astaxanthin is used as a coloring reagent, especially in the industry of farmed fish, such as salmon, because astaxanthin imparts distinctive orange-red coloration to the animals and contributes to consumer appeal in the marketplace.

One of the first steps in the carotenogenic pathway of, e.g. *Phaffia rhodozyma*, is the condensation of two molecules of acetyl-CoA. Acetyl-CoA is also the substrate for acetyl-CoA carboxylase, one of the enzymes involved in fatty acid biosynthesis.

In one aspect, the present invention provides a novel DNA fragment comprising a gene encoding the enzyme acetyl-CoA carboxylase.

More particularly, the present invention provides a DNA containing regulatory regions, such as promoter and terminator, as well as the open reading frame of acetyl-CoA carboxylase gene.

The present invention provides a DNA fragment encoding acetyl-CoA carboxylase in *P. rhodozyma*. The said DNA means a cDNA which contains only open reading frame flanked between the short fragments in its 5'- and 3'-untranslated region, and a genomic DNA which also contains its regulatory sequences such as its promoter and terminator which are necessary for the expression of the acetyl-CoA carboxylase gene in *P. rhodozyma*.

Accordingly, the present invention relates to a polynucleotide comprising a nucleic acid molecule selected from the group consisting of:

(a) nucleic acid molecules encoding at least the mature form of the polypeptide depicted in SEQ ID NO:3;
(b) nucleic acid molecules comprising the coding sequence as depicted in SEQ ID NO:2;
(c) nucleic acid molecules whose nucleotide sequence is degenerate as a result of the genetic code to a nucleotide sequence of (a) or (b);
(d) nucleic acid molecules encoding a polypeptide derived from the polypeptide encoded by a polynucleotide of (a) to (c) by way of substitution, deletion and/or addition of one or several amino acids of the amino acid sequence of the polypeptide encoded by a polynucleotide of (a) to (c);
(e) nucleic acid molecules encoding a polypeptide derived from the polypeptide whose sequence has an identity of 56.3% or more to the amino acid sequence of the polypeptide encoded by a nucleic acid molecule of (a) or (b);
(f) nucleic acid molecules comprising a fragment or a epitope-bearing portion of a polypeptide encoded by a nucleic acid molecule of any one of (a) to (e) and having acetyl-CoA carboxylase activity;
(g) nucleic acid molecules comprising a polynucleotide having a sequence of a nucleic acid molecule amplified from *Phaffia* or *Xanthophylomyces* nucleic acid library using the primers depicted in SEQ ID NO:4, 5, and 6;
(h) nucleic acid molecules encoding a polypeptide having acetyl-CoA carboxylase activity, wherein said polypeptide is a fragment of a polypeptide encoded by any one of (a) to (g);
(i) nucleic acid molecules comprising at least 15 nucleotides of a polynucleotide of any one of (a) to (d);
(j) nucleic acid molecules encoding a polypeptide having acetyl-CoA carboxylase activity, wherein said polypeptide is recognized by antibodies that have been raised against a polypeptide encoded by a nucleic acid molecule of any one of (a) to (h);
(k) nucleic acid molecules obtainable by screening an appropriate library under stringent conditions with a probe having the sequence of the nucleic acid molecule of any one of (a) to (j), and encoding a polypeptide having an acetyl-CoA carboxylase activity;
(l) nucleic acid molecules whose complementary strand hybridizes under stringent conditions with a nucleic acid molecule of any one of (a) to (k), and encoding a polypeptide having acetyl-CoA carboxylase activity.

The terms "gene(s)", "polynucleotide", "nucleic acid sequence", "nucleotide sequence", "DNA sequence" or "nucleic acid molecule(s)" as used herein refers to a polymeric form of nucleotides of any length, either ribonucleotides or deoxyribonucleotides. This term refers only to the primary structure of the molecule.

Thus, this term includes double- and single-stranded DNA, and RNA. It also includes known types of modifications, for example, methylation, "caps" substitution of one or more of the naturally occurring nucleotides with an analog. Preferably, the DNA sequence of the invention comprises a coding sequence encoding the above-defined polypeptide.

A "coding sequence" is a nucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances. SEQ ID:1 depicts the genomic DNA in which the intron sequence is inserted in the coding sequence for acetyl-CoA carboxylase gene from *P. rhodozyma*.

In general, the gene consists of several parts which have different functions from each other. In eukaryotes, genes which encode a corresponding protein, are transcribed to premature messenger RNA (pre-mRNA) differing from the genes for ribosomal RNA (rRNA), small nuclear RNA (snRNA) and transfer RNA (tRNA). Although RNA polymerase II (PolII) plays a central role in this transcription event, PolII can not solely start transcription without cis element covering an upstream region containing a promoter and an upstream activation sequence (UAS), and a trans-acting protein factor. At first, a transcription initiation complex which consists of several basic protein components recognize the promoter sequence in the 5'-adjacent region of the gene to be expressed. In this event, some additional participants are required in the case of the gene which is expressed under some specific regulation, such as a heat shock response, or adaptation to a nutrition starvation, and so on. In such a case, a UAS is required to exist in the 5'-untranslated upstream region around the promoter sequence, and some positive or negative regulator proteins recognize and bind to the UAS. The strength of the binding of transcription initiation complex to the promoter sequence is affected by such a binding of the transacting factor around the promoter, and this enables the regulation of transcription activity.

After the activation of a transcription initiation complex by the phosphorylation, a transcription initiation complex initiates transcription from the transcription start site. Some parts of the transcription initiation complex are detached as an elongation complex from the promoter region to the 3' direction of the gene (this step is called as a promoter clearance event) and the elongation complex continues the transcription until it reaches to a termination sequence that is located in the-3'-adjacent downstream region of the gene. Pre-mRNA thus generated is modified in nucleus by the addition of cap structure at the cap site which almost corresponds to the transcription start site, and by the addition of polyA stretches at the polyA signal which is located at the 3'-adjacent downstream region. Next, intron structures are removed from the coding region and exon parts are combined to yield an open reading frame whose sequence corresponds to the primary amino acid sequence of a corresponding protein. This modification in which a mature mRNA is generated is necessary for a stable gene expression. cDNA in general terms corresponds to the DNA sequence which is reverse-transcribed from this mature mRNA sequence. It can be synthesized by the reverse transcriptase derived from viral species by using a mature mRNA as a template, experimentally.

To express a gene which was derived from eukaryote, a procedure in which cDNA is cloned into an expression vector for *E. coli* is often used. This results from the fact that a specificity of intron structure varies among the organisms and an inability to recognize the intron sequence from other species. In fact, prokaryote has no intron structure in its own genetic background. Even in yeast, the genetic background is different between *Ascomycetes* to which *Saccharomyces cerevisiae* belongs and *Basidiomycetes* to which *P. rhodozyma* belongs, e.g. the intron structure of the actin gene from *P. rhodozyma* cannot be recognized nor spliced by the ascomycetous yeast, *S. cerevisiae*.

Intron structures of some kinds of the genes appear to be involved in the regulation of the expression of their genes. It might be important to use a genomic fragment which has its introns in a case of self-cloning of the gene of a interest whose intron structure involves such a regulation of its own gene expression.

To apply a genetic engineering method for a strain improvement study, it is necessary to study its genetic mechanism in the event such as transcription and translation. It is important to determine a genetic sequence such as its UAS, promoter, intron structure and terminator to study the genetic mechanism.

According to this invention, the gene encoding the acetyl-CoA carboxylase (ACC) gene from *P. rhodozyma* including its 5'- and 3'-adjacent regions as well as its intron structure was determined.

The invention further encompasses polynucleotides that differ from one of the nucleotide sequences shown in SEQ ID NO:2 (and portions thereof) due to degeneracy of the genetic code and also encode an acetyl-CoA carboxylase as that encoded by the nucleotide sequences shown in SEQ ID NO:2. Further the polynucleotide of the invention has a nucleotide sequence encoding a protein having an amino acid sequence shown in SEQ ID NO:3. In a still further embodiment, the polynucleotide of the invention encodes a full length *P. rhodozyma* protein which is substantially homologous to an amino acid sequence of SEQ ID NO:3.

In addition, it will be appreciated by those skilled in the art that DNA sequence polymorphism that lead to changes in the amino acid sequences may exist within a population (e.g., the *P. rhodozyma* population). Such genetic polymorphism in the acetyl-CoA carboxylase gene may exist among individuals within a population due to natural variation.

As used herein, the terms "gene" and "recombinant gene" refer to nucleic acid molecules comprising an open reading frame encoding an acetyl-CoA carboxylase, preferably an acetyl-CoA carboxylase from *P. rhodozyma*.

Such natural variations can typically result in 1-5% variance in the nucleotide sequence of the acetyl-CoA carboxylase gene. Any and all such nucleotide variations and resulting amino acid polymorphism in acetyl-CoA carboxylase that are the result of natural variation and that do not alter the functional activity of acetyl-CoA carboxylase are intended to be within the scope of the invention.

Polynucleotides corresponding to natural variants and non-*P. rhodozyma* homologues of the acetyl-CoA carboxylase cDNA of the invention can be isolated based on their homology to *P. rhodozyma* acetyl-CoA carboxylase polynucleotides disclosed herein using the polynucleotide of the invention, or a portion thereof, as a hybridization probe according to standard hybridization techniques under stringent hybridization conditions. Accordingly, in another embodiment, a polynucleotide of the invention is at least 15 nucleotides in length. Preferably it hybridizes under stringent conditions to the nucleic acid molecule comprising a nucleotide sequence of the polynucleotide of the present invention, e.g. SEQ ID NO:2. In other embodiments, the nucleic acid is at least 20, 30, 50, 100, 250 or more nucleotides in length. The term "hybridizes under stringent conditions" is defined above and is intended to describe conditions for hybridization and washing under which nucleotide sequences at least 60% identical to each other typically remain hybridized to each other. Preferably, the conditions are such that sequences at least about 65% or 70%, more preferably at least about 75% or 80%, and even more preferably at least about 85%, 90% or 95% or more identical to each other typically remain hybridized to each other. Preferably, polynucleotide of the invention that hybridizes under stringent conditions to a sequence of SEQ ID NO:2 corresponds to a naturally occurring nucleic acid molecule.

In the present invention, the polynucleotide sequence includes SEQ ID NO:2 and fragments thereof having polynucleotide sequences which hybridize to SEQ ID NO:2 under stringent conditions which are sufficient to identify specific binding to SEQ ID NO:2. For example, any combination of the following hybridization and wash conditions may be used to achieve the required specific binding:

High Stringent Hybridization: 6×SSC, 0.5% SDS, 100 μg/ml denatured salmon sperm DNA, 50% formamide, incubate overnight with gentle rocking at 42° C.

High Stringent Wash: 1 wash in 2×SSC, 0.5% SDS at room temperature for 15 minutes, followed by another wash in 0.1×SSC, 0.5% SDS at room temperature for 15 minutes.

Low Stringent Hybridization: 6×SSC, 0.5% SDS, 100 μg/ml denatured salmon sperm DNA, 50% formamide, incubate overnight with gentle rocking at 37° C.

Low Stringent Wash: 1 wash in 0.1×SSC, 0.5% SDS at room temperature for 15 minutes.

Moderately stringent conditions may be obtained by varying the temperature at which the hybridization reaction occurs and/or the wash conditions as set forth above. In the present invention, it is preferred to use high stringent hybridization and wash conditions to define the antisense activity against acetyl-CoA carboxylase gene from *P. rhodozyma*.

The term "homology" means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occuring variations, such as sequences from other plant varieties or species, or mutations. These mutations may occur naturally or may be obtained by mutagenesis techniques. The allelic variations may be naturally occurring allelic variants as well as synthetically produced or genetically engineered variants. Structural equivalents can, for example, be identified by testing the binding of said polypeptides to antibodies. Structural equivalents have similar immunological characteristics, e.g. comprise similar epitopes.

As used herein, a "naturally-occurring" nucleic acid molecule refers to an RNA or DNA molecule having a nucleotide sequence that occurs in nature (e.g., encodes a natural protein). Preferably, the polynucleotide encodes a natural *P. rhodozyma* acetyl-CoA carboxylase.

In addition to naturally-occurring variants of the acetyl-CoA carboxylase sequence that may exist in the population, the skilled artisan will further appreciate that changes can be introduced by mutation into a nucleotide sequence of the polynucleotide encoding acetyl-CoA carboxylase, thereby leading to changes in the amino acid sequence of the encoded acetyl-CoA carboxylase, without altering the functional ability of the acetyl-CoA carboxylase. For example, nucleotide substitutions leading to amino acid substitutions at "non-essential" amino acid residues can be made in a sequence of the polynucleotide encoding acetyl-CoA carboxylase, e.g. SEQ ID NO:2. A "non-essential" amino acid residue is a residue that can be altered from the wild-type sequence of one of the acetyl-CoA carboxylase without altering the activity of said acetyl-CoA carboxylase, whereas an "essential" amino acid residue is required for acetyl-CoA carboxylase activity. Other amino acid residues, however, (e.g., those that are not conserved or only semi-conserved in the domain having acetyl-CoA carboxylase activity) may not be essential for activity and thus are likely to be amenable to alteration without altering acetyl-CoA carboxylase activity.

Accordingly, the invention relates to polynucleotides encoding acetyl-CoA carboxylase that contain changes in amino acid residues that are not essential for acetyl-CoA carboxylase activity. Such acetyl-CoA carboxylase differs in amino acid sequence from a sequence contained in SEQ ID NO:3 yet retain the acetyl-CoA carboxylase activity described herein. The polynucleotide can comprise a nucleotide sequence encoding a polypeptide, wherein the polypeptide comprises an amino acid sequence at least about 60% identical to an amino acid sequence of SEQ ID NO:3 and has acetyl-CoA carboxylase activity. Preferably, the protein encoded by the nucleic acid molecule is at least about 60-65% identical to the sequence in SEQ ID NO:3, more preferably at least about 60-70% identical to one of the sequences in SEQ ID NO:3, even more preferably at least about 70-80%, 80-90%, 90-95% homologous to the sequence in SEQ ID NO:3, and most preferably at least about 96%, 97%, 98%, or 99% identical to the sequence in SEQ ID NO:3.

To determine the percent homology of two amino acid sequences (e.g., one of the sequence of SEQ ID NO:3 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences of SEQ ID NO:2 or 3) is occupied by the same amino acid residue or nucleotide as the corresponding position in the other sequence (e.g., a mutant form of the sequence selected), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100). The homology can be determined by computer programs as Blast 2.0 [Altschul, Nuc. Acid. Res., 25:3389-3402 (1997)]. In this invention, GENETYX-SV/RC software (Software Development Co., Ltd., Tokyo, Japan) is used by using its default algorithm as such homology analysis software. This software uses the Lipman-Pearson method for its analytic algorithm.

A nucleic acid molecule encoding an acetyl-CoA carboxylase homologous to a protein with an amino acid sequence of SEQ ID NO:3 can be created by introducing one or more nucleotide substitutions, additions or deletions into a nucleotide sequence of the polynucleotide of the present invention, in particular of SEQ ID NO:2 such that one or more amino acid substitutions, additions or deletions are introduced into the encoded protein. Mutations can be introduced into the sequences of, e.g., SEQ ID NO:2 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an acetyl-CoA carboxylase is preferably replaced with another amino acid residue from the same family. Alternatively, in another embodiment, mutations can be introduced randomly along all or part of an acetyl-CoA carboxylase coding sequence, such as by saturation mutagenesis, and the resultant mutants can be screened for an acetyl-CoA carboxylase activity described herein to identify mutants that retain acetyl-CoA carboxylase activity. Following mutagenesis of one of the sequences of SEQ ID NO:2, the encoded protein can be expressed recombinantly and the activity of the protein can be determined using, for example, assays described herein.

A polynucleotide of the present invention, e.g., a nucleic acid molecule having a nucleotide sequence of SEQ ID NO:2, or a portion thereof, can be isolated using standard molecular biology techniques and the sequence information provided herein. For example, acetyl-CoA carboxylase cDNA can be isolated from a library using all or portion of one of the sequences of the polynucleotide of the present invention as a hybridization probe and standard hybridization techniques. Moreover, a polynucleotide encompassing all or a portion of one of the sequences of the polynucleotide of the present invention can be isolated by the polymerase chain reaction using oligonucleotide primers designed based upon this sequence (e.g., a nucleic acid molecule encompassing all or a portion of one of the sequences of polynucleotide of the present invention can be isolated by the polymerase chain reaction using oligonucleotide primers, e.g. of SEQ ID NO:4, 5, or 6, designed based upon this same sequence of polynucleotide of the present invention. For example, mRNA can be isolated from cells, e.g. *Phaffia* (e.g., by the guanidinium-thiocyanate extraction procedure of Chirgwin et al. and cDNA can be prepared using reverse transcriptase (e.g., Moloney MLV reverse transcriptase or AMV reverse transcriptase available from Promega (Madison, USA)). Synthetic oligonucleotide primers for polymerase chain reaction amplification can be designed based upon one of the nucleotide sequences shown in SEQ ID NO:2. A polynucleotide of the invention can be amplified using cDNA or, alternatively, genomic DNA, as a template and appropriate oligonucleotide primers according to standard PCR amplification techniques. The polynucleotide so amplified can be cloned into an appropriate vector and characterized by DNA sequence analysis. Furthermore, oligonucleotides corresponding to an acetyl-CoA carboxylase nucleotide sequence can be prepared by standard synthetic techniques, e.g., using an automated DNA synthesizer.

The terms "fragment", "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence.

Typically, the truncated amino acid sequence will range from about 5 to about 60 amino acids in length. More typically, however, the sequence will be a maximum of about 50 amino acids in length, preferably a maximum of about 30 amino acids. It is usually desirable to select sequences of at least about 10, 12 or 15 amino acids, up to maximum of about 20 or 25 amino acids.

The term "epitope" relates to specific immunoreactive sites within an antigen, also known as antigenic determinants. These epitopes can be a linear array of monomers in a polymeric composition—such as amino acids in a protein—or consist of or comprise a more complex secondary or tertiary structure. Those of skill will recognize that all immunogens (i. e., substances capable of eliciting an immune response) are antigens; however, some antigen, such as haptens, are not immunogens but may be made immunogenic by coupling to a carrier molecule. The term "antigen" includes references to a substance to which an antibody can be generated and/or to which the antibody is specifically immunoreactive.

The term "one or several amino acids" relates to at least one amino acid but not more than that number of amino acids which would result in a homology of below 60% identity. Preferably, the identity is more than 70% or 80%, more preferred are 85%, 90% or 95%, even more preferred are 96%, 97%, 98%, or 99% identity.

The term "acetyl-CoA carboxylase" or "acetyl-CoA carboxylase activity" relates to enzymatic activities of a polypeptide as described below or which can be determined in enzyme assay method. Furthermore, polypeptides that are inactive in an assay herein but are recognized by an antibody specifically binding to acetyl-CoA carboxylase, i.e., having one or more acetyl-CoA carboxylase epitopes, are also comprised under the term "acetyl-CoA carboxylase". In these cases activity refers to their immunological activity.

The terms "polynucleotide" and "nucleic acid molecule" also relate to "isolated" polynucleotides or nucleic acids molecules. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived.

For example, in various embodiments, the PNO polynucleotide can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Phaffia* cell). Moreover, the polynucleotides of the present invention, in particular an "isolated" nucleic acid molecule, such as a cDNA molecule, can be substantially free of other cellular material, or culture medium when produced by recombinant techniques, or chemical precursors or other chemicals when chemically synthesized.

Preferably, the polypeptide of the invention comprises one of the nucleotide sequences shown in SEQ ID NO:2. The sequence of SEQ ID NO:2 corresponds to the *P. rhodozyma* acetyl-CoA carboxylase cDNAs of the invention.

Further, the polynucleotide of the invention comprises a nucleic acid molecule which is a complement of one of the nucleotide sequences of above mentioned polynucleotides or a portion thereof. A nucleic acid molecule which is complementary to one of the nucleotide sequences shown in SEQ ID NO:2 is one which is sufficiently complementary to one of the nucleotide sequences shown in SEQ ID NO:2 such that it can hybridize to one of the nucleotide sequences shown in SEQ ID NO:2, thereby forming a stable duplex.

The polynucleotide of the invention comprises a nucleotide sequence which is at least about 60%, preferably at least about 65-70%, more preferably at least about 70-80%, 80-90%, or 90-95%, and even more preferably at least about 95%, 96%, 97%, 98%, 99% or more homologous to a nucleotide sequence shown in SEQ ID NO:2, or a portion thereof The polynucleotide of the invention comprises a nucleotide sequence which hybridizes, e.g., hybridizes under stringent conditions as defined herein, to one of the nucleotide sequences shown in SEQ ID NO:2, or a portion thereof.

Moreover, the polynucleotide of the invention can comprise only a portion of the coding region of one of the sequences in SEQ ID NO:2, for example a fragment which can be used as a probe or primer or a fragment encoding a biologically active portion of an acetyl-CoA carboxylase. The nucleotide sequences determined from the cloning of the acetyl-CoA carboxylase gene from *P. rhodozyma* allows for the generation of probes and primers designed for use in identifying and/or cloning acetyl-CoA carboxylase homologues in other cell types and organisms. The probe/primer typically comprises a substantially purified oligonucleotide. The oligonucleotide typically comprises a region of nucleotide sequence that hybridizes under stringent conditions to at least about 12, 15 preferably about 20 or 25, more preferably about 40, 50 or 75 consecutive nucleotides of a sense strand of one of the sequences set forth, e.g., in SEQ ID NO: No:2, an anti-sense sequence of one of the sequences, e.g., set forth in SEQ ID NO:2, or naturally occurring mutants thereof. Primers based on a nucleotide of invention can be used in PCR reactions to clone acetyl-CoA carboxylase homologues. Probes based on the acetyl-CoA carboxylase nucleotide sequences can be used to detect transcripts or genomic sequences encoding the same or homologous proteins. The probe can further comprise a label group attached thereto, e.g. the label group can be a radioisotope, a fluorescent compound, an enzyme, or an enzyme co-factor. Such probes can be used as a part of a genomic marker test kit for identifying cells which express an acetyl-CoA carboxylase, such as by measuring a level of an acetyl-CoA carboxylase-encoding nucleic acid molecule in a sample of cells, e.g., detecting acetyl-CoA carboxylase mRNA levels or determining whether a genomic acetyl CoA carboxylase gene has been mutated or deleted.

The polynucleotide of the invention encodes a polypeptide or portion thereof which includes an amino acid sequence which is sufficiently homologous to an amino acid sequence of SEQ ID NO:3 such that the protein or portion thereof maintains an acetyl-CoA carboxylase activity, in particular an acetyl-CoA carboxylase activity as described in the examples in microorganisms or plants. As used herein, the language "sufficiently homologous" refers to proteins or portions thereof which have amino acid sequences which include a minimum number of identical or equivalent (e.g., an amino acid residue which has a similar side chain as an amino acid residue in one of the sequences of the polypeptide of the present invention amino acid residues to an amino acid sequence of SEQ ID NO:3 such that the protein or portion thereof has an acetyl-CoA carboxylase activity. Examples of an acetyl-CoA carboxylase activity are also described herein.

The protein is at least about 60-65%, preferably at least about 66-70%, and more preferably at least about 70-80%, 80-90%, 90-95%, and most preferably at least about 96%, 97%, 98%, 99% or more homologous to an entire amino acid sequence of SEQ ID NO:3.

Portions of proteins encoded by the acetyl-CoA carboxylase polynucleotide of the invention are preferably biologically active portions of one of the acetyl-CoA carboxylase.

As mentioned herein, the term "biologically active portion of acetyl-CoA carboxylase" is intended to include a portion, e.g., a domain/motif, that has acetyl-CoA carboxylase activity or has an immunological activity such that it is binds to an antibody binding specifically to acetyl-CoA carboxylase. To determine whether an acetyl-CoA carboxylase or a biologically active portion thereof can participate in the metabolism an assay of enzymatic activity may be performed. Such assay methods are well known to those skilled in the art, as detailed in the Examples. Additional nucleic acid fragments encoding biologically active portions of an acetyl-CoA carboxylase can be prepared by isolating a portion of one of the sequences in SEQ ID NO:2, expressing the encoded portion of the acetyl-CoA carboxylase or peptide (e.g., by recombinant expression in vitro) and assessing the activity of the encoded portion of the acetyl-CoA carboxylase or peptide.

At first, a partial gene fragment was cloned containing a portion of the ACC gene by using the degenerate PCR method. Said degenerate PCR is a method to clone a gene of interest which has high homology of amino acid sequence to the known enzyme from other species which has the same or similar function. Degenerate primer, which is used as a primer in degenerate PCR, was designed by a reverse translation of the amino acid sequence to corresponding nucleotides ("degenerated"). In such a degenerate primer, a mixed primer which consists any of A, C, G or T, or a primer containing inosine at an ambiguity code is generally used. In this invention, such mixed primers were used for degenerate primers to clone above gene.

An entire gene containing its coding region with its intron as well as its regulation region such as a promoter or a terminator can be cloned from a chromosome by screening of a genomic library which is constructed in phage vector or plasmid vector in appropriate host, by using a partial DNA fragment obtained by degenerate PCR as described above as a probe after it was labeled. Generally, E. coli as a host strain and E. coli vector, a phage vector such as λ phage vector, or a plasmid vector such as pUC vector is often used in the construction of a library and a following genetic manipulation such as a sequencing, a restriction digestion, a ligation and the like. In this invention, an EcoRI genomic library of P. rhodozyma was constructed in the derivatives of λ vector, λZAPII. An insert size, what length of insert must be cloned, was determined by the Southern blot hybridization for the gene before construction of a library. In this invention, a DNA used for a probe was labeled with digoxigenin (DIG), a steroid hapten instead of conventional $^{32}P$ label, following the protocol which was prepared by the supplier (Boehringer-Mannheim, Mannheim, Germany). A genomic library constructed from the chromosome of P. rhodozyma was screened by using a DIG-labeled DNA fragment which had a portion of a gene of interest as a probe. Hybridized plaques were picked up and used for further study. When λZAPII (insert size was below 9 kb) was used in the construction of the genomic library, in vivo excision protocol was conveniently used for the succeeding step of the cloning into the plasmid vector by using a derivative of single stranded M13 phage, Ex assist phage (Stratagene, La Jolla, USA). A plasmid DNA thus obtained was examined for sequencing.

In this invention, we used the automated fluorescent DNA sequencer, ALFred system (Pharmacia, Uppsala, Sweden) using an autocycle sequencing protocol in which the Taq DNA polymerase is employed in most cases of sequencing.

After the determination of the genomic sequence, a sequence of a coding region was used for a cloning of cDNA of corresponding gene. The PCR method was also exploited to clone cDNA fragment. The PCR primers whose sequences were identical to the sequence at the 5'- and 3'-end of the open reading frame (ORF) were synthesized with an addition of an appropriate restriction site, and PCR was performed by using those PCR primers. In this invention, a cDNA pool was used as a template in this PCR cloning of cDNA. The said cDNA pool consists of various cDNA species which were synthesized in vitro by the viral reverse transcriptase and Taq polymerase (CapFinder Kit manufactured by Clontech, Palo Alto, U.S.A.) by using the mRNA obtained from P. rhodozyma as a template. cDNA of interest thus obtained was confirmed in its sequence. Furthermore, cDNA thus obtained was used for a confirmation of its enzyme activity after the cloning of the cDNA fragment into an expression vector which functions in E. coli under the strong promoter activity such as the lac or T7 expression system.

In another embodiment, the present invention relates to a method for making a recombinant vector comprising inserting a polynucleotide of the invention into a vector.

Further, the present invention relates to a recombinant vector containing the polynucleotide of the invention or produced by said method of the invention.

As used herein, the term "vector" refers to a nucleic acid molecule capable of transporting a polynucleotide to which it has been linked. One type of vector is a "plasmid", which refers to a circular double stranded DNA loop into which additional DNA segments can be ligated. Another type of vector is a viral vector, wherein additional DNA or PNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The present invention also relates to cosmids, viruses, bacteriophages and other vectors used conventionally in genetic engineering that contain a nucleic acid molecule according to the invention. Methods which are well known to those skilled in the art can be used to construct various plasmids and vectors. Alternatively, the nucleic acid molecules and vectors of the invention can be reconstituted into liposomes for delivery to target cells.

The present invention further relates to a vector in which the polynucleotide of the present invention is operatively linked to expression control sequences allowing expression in prokaryotic or eukaryotic host cells. The nature of such control sequences differs depending upon the host organism. In prokaryotes, control sequences generally include promoter, ribosomal binding site, and terminators. In eukaryotes, generally control sequences include promoters, terminators and, in some instances, enhancers, transactivators; or transcription factors.

The term "control sequence" is intended to include, at a minimum, components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is used.

Regulatory sequences include those which direct constitutive expression of a nucleotide sequence in many types of host cell and those which direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by polynucleotides as described herein.

The recombinant expression vectors of the invention can be designed for expression of acetyl-CoA carboxylase in prokaryotic or eukaryotic cells. For example, genes encoding the polynucleotide of the invention can be expressed in bacterial cells such as *E. coli*, insect cells (using baculovirus expression vectors), yeast and other fungal cells, algae, ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially *Stylonychia lemnae* with vectors following, a transformation method as described in WO9801572 and multicellular plant cells. Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc.), pMAL (New England Biolabs, Beverly, USA) and pRIT5 (Pharmacia, Piscataway, USA) which fuse glutathione S-transferase (GST), maltose E binding protein, or protein A, respectively, to the target recombinant protein. In one embodiment, the coding sequence of the polypeptide encoded by the polynucleotide of the present invention is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin, e.g. recombinant acetyl-CoA carboxylase unfused to GST can be recovered by cleavage of the fusion protein with thrombin.

Examples of suitable inducible non-fusion *E. coli* expression vectors include pTrc and pET 11d. Target gene expression from the pTrc vector relies on host RNA polymerase transcription from a hybrid trp-lac fusion promoter. Target gene expression from the pET 11d vector relies on transcription from a T7 gnl0-lac fusion promoter mediated by a coexpressed viral RNA polymerase (T7 gnl). This viral polymerase is supplied by host strains BL21(DE3) or HMS174(DE3) from a resident λ prophage harboring a T7 gnl gene under the transcriptional control of the lacUV 5 promoter.

One strategy to maximize recombinant protein expression is to express the protein in host bacteria with an impaired capacity to proteolytically cleave the recombinant protein. Another strategy is to alter the nucleic acid sequence of the nudeic acid to be inserted into an expression vector so that the individual codons for each amino acid are those preferentially utilized in the batterium chosen for expression, such as *E. coli*. Such alteration of nucleic acid sequences of the invention can be carried out by standard DNA synthesis techniques.

Further, the acetyl-CoA carboxylase vector can be a yeast expression vector. Examples of vectors for expression in yeast *S. cerevisiae* include pYepSec1, pMFa, pJRY88, and pYES2 (Invitrogen, San Diego, USA). Vectors and methods for the construction of vectors appropriate for use in other fungi, such as the filamentous fungi, are known to the skilled artisan.

Alternatively, the polynucleotide of the invention can be introduced in insect cells using baculovirus expression vectors. Baculovirus vectors available for expression of proteins in cultured insect cells (e.g., Sf9 cells) include the pAc series and the pVL series.

Alternatively, the polynucleotide of the invention is introduced in mammalian cells using a mammalian expression vector. Examples of mammalian expression vectors include pCDM8 and pMT2PC. When used in mammalian cells, the expression vector's control functions are often provided by viral regulatory elements. For example, commonly used promoters are derived from polyoma, Adenovirus 2, cytomegalovirus and Simian Virus 40.

The recombinant mammalian expression vector can be capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific), lymphoid-specific promoters, in particular promoters of T cell receptors and immunoglobulins, neuron-specific promoters (e.g., the neurofilament promoter), pancreas-specific promoters, and mammary gland-specific promoters (e.g., milk whey promoter; U.S. Pat. No. 4,873, 316 and EP 264,166). Developmentally-regulated promoters are also encompassed, for example the murine hox promoters and the fetoprotein promoter.

Thus expressed ACC gene can be verified for its activity, e.g., by an enzyme assay method. Some experimental protocols are described in the literature. The following is the one of the methods which is used for the determination of acetyl-CoA carboxylase activity: Assays are performed by measuring the loss in acetyl-CoA and/or the production of malonyl-CoA at 5 min intervals for 20 min, using reverse phase HPLC. The rate of conversion of acetyl-CoA to malonyl-CoA is found to be linear for 20 min, and velocities are calculated by linear regression analysis of the malonyl-CoA concentration with respect to time. The reaction mixture contained 50 µM Tris, pH 7.5, 6 µM acetyl-CoA, 2 mM ATP, 7 mM $KHCO_3$, 8 mM $MgCl_2$, 1 mM dithiothreitol, and 1 mg/ml bovine serum albumin. Enzyme is preincubated (30 min, 25° C.) with bovine serum albumin (2 mg/ml) and potassium citrate (10 mM). Reactions are initiated by transferring 50 µl of preincubated enzyme to the reaction mixture (final volume 200 µl) and incubated for 5-20 min at 25° C. Reactions are terminated by addition of 50 µl 10% perchloric acid. Following termination of the reaction, the samples are centrifuged (3 min, 10,000×g) and analyzed by HPLC. A mobile phase of 10 mM $KH_2PO_4$, pH 6.7 (solvent A), and MeOH (solvent B) is used. The flow rate is 1.0 ml/min, and the gradient is as follows: hold at 100% solvent A for 1 min followed by a linear gradient to 30% solvent B over the next 5 min, then hold at 30% solvent B for 5 min. Using this method the retention times were 7.5 and 9.0 min for malonyl-CoA and acetyl-CoA, respectively. When an expression vector for *S. cerevisiae* is used, a complementation analysis can be conveniently exploited by using conditional acetyl-CoA carboxylase null mutant strain derived from *S. cerevisiae* as a host strain for its confirmation of activity.

Succeeding to the confirmation of the enzyme activity, an expressed protein would be purified and used for raising the antibody against the purified enzyme. Antibody thus prepared would be used for a characterization of the expression of the corresponding enzyme in a strain improvement study, an optimization study of the culture condition, and the like.

In a further embodiment, the present invention relates to an antibody that binds specifically to the polypeptide of the present invention or parts, i.e. specific fragments or epitopes of such a protein.

The antibodies of the invention can be used to identify and isolate other acetyl-CoA carboxylase and genes. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described by Kohler and Milstein, which comprise the fusion of mouse myeloma cells to spleen cells derived from immunized mammals.

Furthermore, antibodies or fragments thereof to the aforementioned peptides can be obtained by using methods known to the skilled person. These antibodies can be used, for example, for the immunoprecipitation and immunolocalization of proteins according to the invention as well as for the monitoring of the synthesis of such proteins, for example, in recombinant organisms, and for the identification of compounds interacting with the protein according to the invention. For example, surface plasmon resonance as employed in the BIAcore system can be used to increase the efficiency of phage antibodies selections, yielding a high increment of affinity from a single library of phage antibodies which bind to an epitope of the protein of the invention. In many cases, the binding phenomenon of antibodies to antigens is equivalent to other ligand/anti-ligand binding.

In this invention, the gene fragment for acetyl-CoA carboxylase was cloned from *P. rhodozyma* with a purpose to decrease its expression level in *P. rhodozyma* by genetic method using the cloned gene fragment.

To decrease a gene expression with genetic methods, some strategies can be employed, one of which is a gene-disruption method. In this method, a partial fragment of the objective gene to be disrupted is ligated to a drug resistant cassette on the integration vector which can not replicate in the host organism. A drug resistance gene which encodes the enzyme that enables the host to survive in the presence of a toxic antibiotic is often used for the selectable marker. G418 resistance gene harbored in pGB-Ph9 (Wery et al. (Gene, 184, 89-97, 1997)) is an example of a drug resistance gene which functions in *P. rhodozyma*. Nutrition complementation marker can be also used in the host which has an appropriate auxotrophy marker. *P. rhodozyma* ATCC24221 strain that requires cytidine for its growth is one example of the auxotroph. By using CTP synthetase as donor DNA for ATCC24221, a host vector system using a nutrition complementation can be established.

After the transformation of the host organisms and recombination between the objective gene fragment on the vector and its corresponding gene fragment on the chromosome of the host organisms, the integration vector is integrated onto the host chromosome by single cross recombination. As a result of this recombination, the drug resistant cassette would be inserted in the objective gene whose translated product is only synthesized in its truncated form which does not have its enzymatic function. In a similar manner, two parts of the objective gene were also used for gene disruption study in which the drug resistant gene can be inserted between such two partial fragments of the objective genes on the integration vector. In the case of this type of vector, double recombination event between the gene fragments harbored on the integration vector and the corresponding gene fragments on the chromosome of the host are expected. Although frequency of this double crossing-over recombination is lower than single cross recombination, null, phenotype of the objective gene by the double cross recombination is more stable than by the single cross recombination.

On the other hand, this strategy has difficulty in the case of the gene whose function is essential and disruption is lethal for the host organism such as acetyl-CoA carboxylase gene. The function of acetyl-CoA carboxylase is indispensable for the host survival other than the biosynthesis of fatty acid. From such a viewpoint, it seemed to be difficult to construct the acetyl-CoA carboxylase disruptant from P. rhodozyma by this gene disruption method.

In such a case, other strategies can be applied to decrease (not to disrupt) a gene expression, one of which is a conventional mutagenesis to screen the mutant whose expression for acetyl-CoA carboxylase is decreased. In this method, an appropriate recombinant in which an appropriate reporter gene is fused to the promoter region of acetyl-CoA carboxylase gene from the host organism is mutated and mutants which show a weaker activity of reporter gene product can be screened. In such mutants, it is expected that their expression of acetyl-CoA carboxylase activity decreased by the mutation lying in the promoter region of reporter gene or trans-acting region which might affect the expression of acetyl-CoA carboxylase gene other than the mutation lying in the promoter gene itself In the case of mutation occurring at the promoter region of the reporter fusion, such mutation can be isolated by the sequence of the corresponding region. Thus isolated mutation can be introduced in a variety of carotenoids, especially astaxanthin producing mutants derived from P. rhodozyma by a recombination between the original promoter for acetyl-CoA carboxylase gene on the chromosome and the mutated promoter fragment. To exclude mutations occurring at a trans-acting region, a mutation can also be induced by an in vitro mutagenesis of a cis element in the promoter region. In this approach, a gene cassette, containing a reporter gene which is fused to a promoter region derived from a gene of interest at its 5'-end and a terminator region from a gene of interest at its 3'-end, is mutagenized and then introduced into P. rhodozyma. By detecting the difference of the activity of the reporter gene, an effective mutation can be screened. Such a mutation can be introduced in the sequence of the native promoter region on the chromosome by the same method as the case of an in vivo mutation approach. But, these methods have some drawbacks to have some time-consuming process.

Another strategy to decrease a gene expression is an antisense method. This method is frequently applied to decrease the gene expression even when teleomorphic organisms such as P. rhodozyma are used as host organisms, to which the mutation and gene disruption method is usually difficult to be applied. The anti-sense method is a method to decrease an expression of gene of interest by introducing an artificial gene fragment, whose sequence is complementary to cDNA fragment of the gene of interest. Such an anti-sense gene fragment would form a complex with a mature mRNA fragment of the objective gene in vivo and inhibit an efficient translation from mRNA, as a consequence.

An "antisense" nucleic acid molecule comprises a nucleotide sequence which is complementary to a "sense" nucleic acid molecule encoding a protein, e. g., complementary to the coding strand of a double-stranded cDNA molecule or complementary to a mRNA sequence. Accordingly, an anti-sense nucleic acid molecule can hydrogen bond to a sense nucleic acid molecule. The antisense nucleic acid molecule can be complementary to an entire acetyl-CoA carboxylase-coding strand, or to only a portion thereof. Accordingly, an antisense nucleic acid molecule can be antisense to a "coding region" of the coding strand of a nucleotide sequence encoding an acetyl-CoA carboxylase. The term "coding region" refers to the region of the nucleotide sequence comprising codons which are translated into amino acid residues. Further, the antisense nucleic acid molecule is antisense to a "noncoding region" of the coding strand of a nucleotide sequence encoding acetyl-CoA carboxylase. The term "noncoding region" refers to 5' and 3' sequences which flank the coding region that are not translated into a polypeptide (i.e., also referred to as 5' and 3' untranslated regions).

Given the coding strand sequences encoding acetyl-CoA carboxylase disclosed herein, antisense nucleic acid molecules of the invention can be designed according to the rules of Watson and Crick base pairing. The antisense nucleic acid molecule can be complementary to the entire coding region of acetyl-CoA carboxylase mRNA, but can also be an oligonucleotide which is antisense to only a portion of the coding or noncoding region of acetyl-CoA carboxylase mRNA. For example, the antisense oligonucleotide can be complementary to the region surrounding the translation start site of acetyl-CoA carboxylase mRNA. An antisense oligonucleotide can be, for example, about 5, 10, 15, 20, 25, 30, 35, 40, 45 or 50 nucleotides in length. An antisense nucleic acid molecule of the invention can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the anti-sense nucleic acid include 5-fluorouracil, 5-bromouracil, 5-chlorouracil, 5-iodouracil, hypoanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine; 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a polynucleotide has been subcloned in an antisense orientation (i.e., RNA transcribed from the inserted polynucleotide will be of an antisense orientation to a target polynucleotide of interest, described further in the following subsection).

The antisense nucleic acid molecules of the invention are typically administered to a cell or generated in situ such that they hybridize with or bind to cellular mRNA and/or genomic DNA encoding an acetyl-CoA carboxylase to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The anti-sense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

The antisense nucleic acid molecule of the invention may, e.g., be an α-anomeric nucleic acid molecule. An α-anomeric nucleic acid molecule forms specific double-stranded hybrids with complementary RNA in which, contrary to the usual β-units, the strands run parallel to each other. The antisense nucleic acid molecule can also comprise a 2'-o-methylribonucleotide or a chimeric RNA-DNA analogue.

Further the antisense nucleic acid molecule of the invention can be a ribozyme. Ribozymes are catalytic RNA molecules with ribonuclease activity which are capable of cleaving a single-stranded nucleic acid, such as a mRNA, to which they have a complementary region. Thus, ribozymes (e.g., hammerhead ribozymes) can be used to catalytically cleave acetyl-CoA carboxylase mRNA transcripts to thereby inhibit translation of mRNA. A ribozyme having specificity for an acetyl-CoA carboxylase-encoding nucleic acid molecule can be designed based upon the nucleotide sequence of an acetyl-CoA carboxylase cDNA disclosed herein or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an encoding mRNA (see, e.g., U.S. Pat. Nos. 4,987,071 and 5,116,742). Alternatively, acetyl-CoA carboxylase mRNA can be used to select a catalytic RNA having a specific ribonuclease activity from a pool of RNA molecules.

The application of the antisense method to construct a carotenoid overproducing strain from P. rhodozyma is disclosed in EP 1,158,051.

In one embodiment the present invention relates to a method of making a recombinant host cell comprising introducing the vector or the polynucleotide of the present invention into a host cell.

Vector DNA can be introduced into prokaryotic or eukaryotic cells via conventional transformation or transfection techniques. As used herein, the terms "transformation" and "transfection", conjugation and transduction are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells are known to the skilled artisan.

For stable transfection of mammalian cells, only a small fraction of cells may integrate the foreign DNA into their genome, depending upon the expression vector and transfection technique used. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the polypeptide of the present invention or can be introduced on a separate vector. Cells stably transfected with the introduced nucleic acid can be identified by, for example, drug selection (e.g;, cells that have incorporated the selectable marker gene will survive, while the other cells die).

To create a homologous recombinant microorganism, a vector is prepared which contains at least a portion of the polynucleotide of the present invention into which a deletion, addition or substitution has been introduced to thereby alter, e.g., functionally disrupt, the acetyl-CoA carboxylase gene. Preferably, this acetyl-CoA carboxylase gene is a P. rhodozyma acetyl-CoA carboxylase gene, but it can be a homologue from a related or different source. Alternatively, the vector can be designed such that, upon homologous recombination, the endogenous acetyl-CoA carboxylase gene is mutated or otherwise altered but still encodes a functional protein (e.g., the upstream regulatory region can be altered to thereby alter the expression of the endogenous acetyl-CoA carboxylase). To create a point mutation via homologous recombination also DNA-RNA hybrids can be used known as chimeraplasty known from Cole-Strauss et al., Nucl. Aci. Res., 27, 5, 1323-1330, 1999 and Kmiec, Gene therapy., American Scientist. 87, 3, 240-247. 1999.

The vector is introduced into a cell and cells in which the introduced polynucleotide gene has homologously recombined with the endogenous acetyl-CoA carboxylase gene are selected, using art-known techniques.

Further host cells can be produced which contain selection systems which allow for regulated expression of the introduced gene. For example, inclusion of the polynucleotide of the invention on a vector placing it under control of the lac operon permits expression of the polynucleotide only in the presence of IPTG. Such regulatory systems are well known in the art.

Preferably, the introduced nucleic acid molecule is foreign to the host cell.

By "foreign" it is meant that the nucleic acid molecule is either heterologous with, respect to the host cell, this means derived from a cell or organism with a different genomic background, or is homologous with respect to the host cell but located in a different genomic environment than the naturally occurring counterpart of said nucleic acid molecule. This means that, if the nucleic acid molecule is homologous with respect to the host cell, it is not located in its natural location in the genome of said host cell, in particular it is surrounded by different genes. In this case the nucleic acid molecule may be either under the control of its own promoter or under the control of a heterologous promoter. The vector or nucleic acid molecule according to the invention which is present in the host cell may either be integrated into the genome of the host cell or it may be maintained in some form extrachromosomally. In this respect, it is also to be understood that the nucleic acid molecule of the invention can be used to restore or ceate a mutant gene via homologous recombination.

Accordingly, in another embodiment the present invention relates to a host cell genetically engineered with the polynucleotide of the invention or the vector of the invention.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

For example, a polynucleotide of the present invention can be introduced in bacterial cells as well as insect cells, fungal cells or mammalian cells (such as Chinese hamster ovary cells (CHO) or COS cells), algae, ciliates, plant cells, fungi or other microorganims like E. coli. Other suitable host cells are known to those skilled in the art. Preferred are E. coli, baculovirus, Agrobacterium or fungal cells are, for example, those of the genus Saccharomyces, e.g. those of the species S. cerevisiae or P. rhodozyna (Xanthophylomyces dendrorhous).

In addition, in one embodiment, the present invention relates to a method for the production of fungal transformants comprising the introduction of the polynucleotide or the vector of the present invention into the genome of said fungal cell.

For the expression of the nucleic acid molecules according to the invention in sense or antisense orientation in plant cells, the molecules are placed under the control of regulatory elements which ensure the expression in fungal cells. These regulatory elements may be heterologous or homologous with respect to the nucleic acid molecule to be expressed as well with respect to the fungal species to be transformed.

In general, such regulatory elements comprise a promoter active in fungal cells. To obtain constitutive expression in fungal cells, preferably constitutive promoters are used, e.g., the glyceraldehyde-3-dehydrogenase promoter derived from P. rhodozyma (WO 97/23,633). Inducible promoters may be used in order to be able to exactly control expression. An example for inducible promoters is the promoter of genes encoding heat shock proteins. Also an amylase gene promoter which is a candidate for such inducible promoters has been described (EP 1,035,206). The regulatory elements may further comprise transcriptional and/or translational enhancers functional in fungal cells. Furthermore, the regulatory elements may include transcription termination signals, such as a poly-A signal, which lead to the addition of a poly A tail to the transcript which may improve its stability.

Methods for the introduction of foreign DNA into fungal cells are also well known in the art. These include, for example, transformation with the LiCl method, the fusion of protoplasts, electroporation, biolistic methods like particle bombardment other methods known in the art. Methods for the transformation using biolistic methods are well known to the person skilled in the art.

The term "transformation" as used herein, refers to the transfer of an exogenous polynucleotide into a host cell, irrespective of the method used for the transfer. The polynucleotide may be transiently or stably introduced into the host cell and may be maintained non-integrated, for example, as a plasmid or as chimeric links, or alternatively, may be integrated into the host genome.

In general, the fungi which can be modified according to the invention and which either show overexpression of a protein according to the invention or a reduction of the synthesis of such a protein can be derived from any desired fungal species.

Further, in one embodiment, the present invention relates to a fungal cell comprising the polynucleotide the vector or obtainable by the method of the present invention.

Thus, the present invention relates also to transgenic fungal cells which contain (preferably stably integrated into the genome) a polynucleotide according to the invention linked to regulatory elements which allow expression of the polynucleotide in fungal cells and wherein the polynucleotide is foreign to the transformed fungal cell. For the meaning of foreign; see supra.

Thus, the present invention also relates to transformed fungal cells according to the invention.

Accordingly, due to the altered expression of acetyl-CoA carboxylase, cells metabolic pathways are modulated in yield production, and/or efficiency of production.

The terms "production" or "productivity" are art-recognized and include the concentration of the fermentation product (for example fatty acids, carotenoids, (poly)saccharides, lipids, vitamins, isoprenoids, wax esters, and/or polymers like polyhydroxyalkanoates and/or its metabolism products or further desired fine chemical as mentioned herein) formed within a given time and a given fermentation volume (e.g., kg product per hour per liter).

The term "efficiency" of production includes the time required for a particular level of production to be achieved (for example, how long it takes for the cell to attain a particular rate of output of a said altered yield, in particular, into carotenoids, (poly)saccharides, lipids, vitamins, isoprenoids etc.).

The term "yield" or "product/carbon yield" is art-recognized and includes the efficiency of the conversion of the carbon source into the product (i.e. acetyl CoA, fatty acids, vitamins, carotenoids, isoprenoids, lipids etc. and/or further compounds as defined above and which biosynthesis is based on said products). This is generally written as, for example, kg product per kg carbon source. By increasing the yield or production of the compound, the quantity of recovered molecules, or of useful recovered molecules of that compound in a given amount of culture over a given amount of time is increased.

The terms "biosynthesis" (which is used synonymously for "synthesis" of "biological production" in cells, tissues plants, etc.) or a "biosynthetic pathway" are art-recognized and include the synthesis of a compound, preferably an organic compound, by a cell from intermediate compounds in what may be a multistep and highly regulated process.

The language "metabolism" is art-recognized and includes the totality of the biochemical reactions that take place in an organism. The metabolism of a particular compound, then, (e.g., the metabolism of acetyl CoA, a fatty acid, hexose, isoprenoid, vitamin, carotenoid, lipid etc.) comprises the overall biosynthetic, modification, and degradation pathways in the cell related to this compound.

Such a genetically engineered P. rhodozyma would be cultivated in an appropriate medium and evaluated in its productivity of carotenoids, especially astaxanthin. A hyper producer of astaxanthin thus selected would be confirmed in view of the relationship between its productivity and the level of gene or protein expression which is introduced by such a genetic engineering method.

The present invention is further illustrated with Examples described below.

The following materials and methods employed in the Examples are described below:

Strains

P. rhodozyma ATCC96594 (re-deposited under the accession No. ATCC 74438 on Apr. 8, 1998 pursuant to the Budapest Treaty)

E. coli DH5α: F$^-$, φ80d, lacZΔM15, Δ(lacZYA-argF)U169, hsd ($r_K^-$, $m_K^+$), recA1, endA1, deoR, thi-1, supE44, gyrA96, relA1 (Toyobo, Osaka, Japan)

E. coli XL1-Blue MRF': Δ(mcrA)183, Δ(mcrCB-hsdSMR-mrr)173, endA1, supE44, thi-1, recA1, gyrA96, relA1, lac [F' proAB, lacIqZΔM15, Tn10 (tet$^r$)] (Stratagene, La Jolla, USA)

E. coli SOLR: e14-(mcrA), Δ(mcrCB-hsdSMR-mrr)171, sbcC, recB, recJ, umuC:Tn5(kan$^r$), uvrC, lac, gyrA96, relA1, thi-1, endA1, ΔR, [F' proAB, lacIqZ ΔM15] Su- (nonsuppressing) (Stratagene)

E. coli TOP10: F-, mcrA, Δmrr-hsdRMS-mcrBC), φ80, ΔlacZ M15, ΔlacX74, recA1, deoR, araD139, (ara-leu) 7697, galU, galK, rpsL (Str$^r$), endA1, nupG (Invitrogen, Carlsbad, USA)

Vectors

λZAPII (Stratagene)

pBluescriptII KS- (Stratagene)

pMOSBlue T-vector (Amersham, Buckinghamshire, U.K.)

pCR2.1-TOPO (Invitrogen)

Media

P. rhodozyma strain was maintained routinely in YPD medium (DIFCO, Detroit, U.S.A.).

E. coli strain was maintained in LB medium (10 g Bacto-trypton, 5 g yeast extract (DIFCO) and 5 g NaCl per liter). NZY medium (5 g NaCl, 2 g MgSO$_4$-7H$_2$O, 5 g yeast extract (DIFCO), 10 g NZ amine type A (WAKO, Osaka, Japan) per liter) is used for λ phage propagation in a soft agar (0.7% agar (WAKO)). When an agar medium was prepared, 1.5% of agar (WAKO) was supplemented.

Methods

Restriction enzymes and T4 DNA ligase were purchased from Takara Shuzo (Ohtsu, Japan).

Isolation of a chromosomal DNA from P. rhodozyma was performed by using QIAGEN Genomic Kit (QIAGEN, Hilden, Germany) following the protocol supplied by the manufacturer. Mini-prep of plasmid DNA from transformed E. coli was performed with the Automatic DNA isolation system (PI-50, Kurabo, Co. Ltd., Osaka, Japan). Midi-prep of plasmid DNA from an E. coli transformant was performed by using QIAGEN column (QIAGEN). Isolation of λ DNA was performed by Wizard lambda preps DNA purification system (Promega, Madison, U.S.A.) following the protocol prepared by the manufacturer. A DNA fragment was isolated and purified from agarose by using QIAquick or QIAEX II (QIAGEN). Manipulation of λ phage derivatives was followed by the protocol prepared by the manufacturer (Stratagene).

Isolation of total RNA from P. rhodozyma was performed with the phenol method by using Isogen (Nippon Gehe; Toyama, Japan): mRNA was purified from total RNA thus obtained by using mRNA separation kit (Clontech). cDNA was synthesized by using CapFinder cDNA construction kit (Clontech).

In vitro packaging was performed by using Gigapack III gold packaging extract (Stratagene).

The polymerase chain reaction (PCR) was performed with the thermal cycler from Perkin Elmer model 2400. Each PCR condition is described in examples. PCR primers were purchased from a commercial supplier. Fluorescent DNA primers for DNA sequencing were purchased from Pharmacia. DNA sequencing was performed with the automated fluorescent DNA sequencer (ALFred, Pharmacia).

Competent cells of DH5α were purchased from Toyobo (Japan).

EXAMPLE 1

Isolation of mRNA from P. rhodozyma and Construction of cDNA Library

To construct cDNA library of P. rhodozyma, total RNA was isolated by phenol extraction method right after the cell disruption and the mRNA from P. rhodozyma ATCC96594 strain was purified by using mRNA separation kit (Clontech).

At first, Cells of ATCC96594 strain from 10 ml of two-day-culture in YPD medium were harvested by centrifugation (1500×g for 10 min.) and washed once with extraction buffer (10 mM Na-citrate/HCl (pH 6.2) containing 0.7 M KCl). After suspending in 2.5 ml of extraction buffer, the cells were disrupted by French press homogenizer (Ohtake Works Corp., Tokyo, Japan) at 1500 kgf/cm2 and immediately mixed with two times of volume of isogen (Nippon gene) according to the method specified by the manufacturer. In this step, 400 μg of total RNA was recovered.

Then, this total RNA was purified by using mRNA separation kit (Clontech) according to the method specified by the manufacturer. Finally, 16 μg of mRNA from P. rhodozyma ATCC96594 strain was obtained.

To construct cDNA library, CapFinder PCR cDNA construction kit (Clontech) was used according to the method specified by the manufacturer. One μg of purified mRNA was applied for a first strand synthesis followed by PCR amplification. After this amplification by PCR, 1 mg of cDNA pool was obtained.

EXAMPLE 2

Cloning of a Partial ACC (acetyl-CoA carboxylase) Gene from P. rhodozyma

To clone a partial ACC gene from P. rhodozyma, a degenerate PCR method was exploited. Species and accession number to database whose sequence for acetyl-CoA carboxylase were used for multiple alignment analysis are as follows.

| | |
|---|---|
| Arabidopsis thaliana | D34630 (DDBJ) |
| Emericella nidulans | Y15996 (EMBL) |
| Gallus gallus | P11029 (Swiss-Prot) |
| Glycine max | L48995 (GenBank) |
| Homo sapiens | S41121 (PIR) |
| Medicago sativa | L25042 (GenBank) |
| Ovis aries | Q28559 (Swiss-Prot) |
| Rattus norvegicus | P11497 (Swiss-Prot) |
| Saccharomyces cerevisiae | Q00955 (Swiss-Prot) |
| Schizosaccharomyces pombe | P78820 (Swiss-Prot) |
| Ustilago maydis | S49991 (PIR) |

Two mixed primers whose nucleotide sequences were designed and synthesized based on the common sequence of known acetyl-CoA carboxylase genes from other species: acc9 (sense primer) (SEQ ID NO:4) and acc13 (antisense primer) (SEQ ID NO:5) (in the sequences "n" means nucleotides a, c, g or t, "h" means nucleotides a, c or t, "m" means nucleotides a or c, "k" means nucleotides g or t, and "y" means nucleotides c or t). After the PCR reaction of 25 cycles of 95° C. for 30 seconds, 45° C. for 30 seconds and 72° C. for 15 seconds by using ExTaq (Takara Shuzo) as a DNA polymerase and cDNA pool obtained in Example 1 as a template, reaction mixture was applied to agarose gel electrophoresis. One PCR band that had a desired length (0.8 kb) was recovered from the agarose gel and purified by QIAquick (QIAGEN) according to the method by the manufacturer and then ligated to pMOSBlue-T-vector (Amersham). After transformation of competent E. coli DH5α, 6 white colonies were selected and plasmids were isolated with Automatic DNA isolation system. As a result of sequencing, it was found that 3 clones had a sequence whose deduced amino acid sequence was similar to known acetyl-CoA carboxylase genes. These isolated cDNA clones were designated as pACC1014 and used for further screening study.

EXAMPLE 3

Isolation of Genomic DNA from P. rhodozyma

To isolate a genomic DNA from P. rhodozyma, QIAGEN genomic kit was used according to the method specified by the manufacturer.

At first, cells of P. rhodoyma ATCC96594 strain from 100 ml of overnight culture in YPD medium were harvested by centrifigation (1500×g for 10 min.) and washed once with TE buffer (10 mM Tris/HCl (pH 8.0) containing 1 mM EDTA). After suspending in 8 ml of Y1 buffer of the QIAGEN genomic kit, lyticase (SIGMA, St. Louis, U.S.A.) was added at the concentration of 2 mg/ml to disrupt cells by enzymatic degradation and the reaction mixture was incubated for 90 min at 30° C. and then proceeded to the next extraction step.

Finally, 20 µg of genomic DNA was obtained.

EXAMPLE 4

Southern Blot Hybridization by using pACC1014 as a Probe

Southern blot hybridization was performed to clone a genomic fragment which contains ACC gene from P. rhodozyma. Two µg of genomic DNA was digested by EcoRI and subjected to agarose gel electrophoresis followed by acidic and alkaline treatment. The denatured DNA was transferred to nylon membrane (Hybond N+, Amersham) by using transblot (Joto Rika, Tokyo, Japan) for an hour. The DNA which was transferred to nylon membrane was fixed by a heat treatment (80° C., 90 min). A probe was prepared by labeling a template DNA (EcoRI and SalI-digested pACC1014) with DIG multipriming method (Boehringer Mannheim). Hybridization was performed with the method specified by the manufacturer. As a result, a hybridized band was visualized in the range from 2.0 to 2.3 kilobases (kb).

EXAMPLE 5

Cloning of a Genomic Fragment Containing the ACC Gene

4 µg of the genomic DNA were digested by EcoRI and subjected to agarose gel electrophoresis. Then, DNAs with a length within the range from 1.5 to 2.7 kb was recovered by QIAEX II gel extraction kit (QIAGEN) according to the method specified by the manufacturer. The purified DNA was ligated to 0.5 µg of EcoRI-digested and CIAP (calf intestine alkaline phosphatase)-treated λZAP II (Stratagene) at 16° C. overnight, and packaged by Gigapack III gold packaging extract (Stratagene). The packaged extract was infected to E. coli MRF' strain and over-laid with NZY medium poured onto LB agar medium. About 5000 plaques were screened by using EcoRI and SalI-digested pACC1014 as a probe. Five plaques were hybridized to the labeled probe.

The in vivo excision protocol was applied to these λZAP II derivatives containing putative ACC gene from P. rhodozyma by following the instruction manual (Stratagene) to clone the insert fragment into E. coli cloning vector, pBluescript SK. Each clone recovered from five positive plaques was subjected for sequencing analysis and it was found that the three of them had the identical sequence to the insert fragment of pACC1014. One of the clone was named as pACC1224 and used for further study. As a result of whole sequencing of the entire region of insert fragment in pACC1224, it was suggested that this clone contained neither its 5'- nor 3'-end of the ACC gene.

EXAMPLE 6

Cloning of the Flanking Region of the Insert Fragment in pACC1224 from the Genome of P. rhodozyma by Genome Walking Method Two PCR primers were synthesized based on the internal sequence of pACC1224 and used for the genome walking method: acc17 (SEQ ID NO:6) and acc18 (SEQ ID NO:7). The protocol of the instruction manual provided from the supplier (Clontech) was followed for the genome walking method. In the PCR reaction using acc17 primer, a 2.8 kb PCR band emerged from the genomic StuI library. In the case of acc18 primer, a 2.2 kb PCR band was produced in the genomic PvuII library. These PCR bands were cloned into pCR2.1-TOPO (Invitrogen) and it was revealed that 2.8 kb PCR band contained a 5' fragment of ACC gene and 2.2 kb PCR band contained 3' fragment of ACC gene, respectively. The clones containing 2.8 kb and 2.2 kb PCR fragment were named as pACCStu107 and pACCPvd107, respectively and used for further study.

EXAMPLE 7

Southern Blot Hybridization by using pACCStu107 and pACCPvd107 as Probes

Southern blot hybridization was performed to clone a genomic fragment which covered the ACC gene from P. rhodozyma. 2 µg of genomic DNA was digested by EcoRI and subjected to agarose gel electrophoresis followed by acidic and alkaline treatment. The denatured DNA was transferred to nylon membrane (Hybond N+, Amersham) by using transblot (Joto Rika, Tokyo, Japan) for an hour. The DNA which was transferred to nylon membrane was fixed by a heat treatment (80° C., 90 min). A probe was prepared by labeling a template DNA (EcoRI-digested pACCStu107 and pACCPvd107) with the DIG multi-priming method (Boehringer Mannheim). Hybridization was performed with the method specified by the manufacturer. As a result, several hybridized bands whose size was close to 2.0 kb, 0.9 kb and 0.6 kb were visualized when the insert fragment in pACCStu107 was used as a probe. In the case that the insert fragment in pACCPvd107 was used as a probe, a hybridized band was visualized in the range from 6.0 kb to 6.5 kb.

EXAMPLE 8

Cloning of the Genomic Clone Covering the ACC Gene

In a similar manner to Example 5, the genomic fragment containing the insert fragment in pACCStu107 and pACCPvd107 was cloned by plaque hybridization. 4 μg of the genomic DNA was digested by EcoRI and subjected to agarose gel electrophoresis. Then, DNAs with a length within the following range were recovered by QIAEX II gel extraction kit (QIAGEN) according to the method specified by the manufacturer: (1) from 2.7 to 5.0 kb; (2) from 1.4 to 2.7 kb; and (3) from 0.5 to 1.4 kb.

Each purified DNA was ligated to 0.5 μg of EcoRI-digested and CIAP (calf intestine alkaline phosphatase)-treated λZAP II (Stratagene) at 16° C. overnight, and packaged by Gigapack III gold packaging extract (Stratagene). The packaged extract was infected to *E. coli* MRF' strain and over-laid with NZY medium poured onto LB agar medium. About 5000 plaques were screened by using EcoRI-digested pACCStu107 and pACCPvd107 as probes.

The following candidates were isolated after plaque hybridization study.
1) 3 plaques from the 2.7 to 6.0 kb library by using the insert of pACCPvd107 as a probe.
2) 3 plaques from the 1.4 to 2.7 kb library by using the insert of pACCStu107 as a probe.
3) 21 plaques from the 0.5 to 1.4 kb library by using the insert of pACCStu107 as a probe.

The in vivo excision protocol was applied to these λZAP II derivatives containing putative ACC gene from *P. rhodozyma* by following the instruction manual (Stratagene) to clone the insert fragment into *E. coli* cloning vector, pBluescript SK. Each clone recovered from the positive plaques was subjected for sequencing analysis. At least each clone had the putative ACC gene from BLAST X analysis (http://www.blast.genome.ad.jp/). The following clones were selected and used for further analysis:

pACC119-18 having a 6 kb insert and covering the 3' end of the ACC gene;
pACC119-17-0.6 having a 0.6 kb insert flanking the 5' end of the pACC1224 insert fragment;
pACC119-17-2 having a 2 kb insert flanking the 5' end of the pACC119-17-0.6 insert fragment; and
pACC127-17-0.9 having a 0.9 kb insert flanking the 5' end of the pACC119-17-2 insert fragment.

As a result of whole sequencing of the entire region of insert fragment in pACC119-18, pACC119-17-0.6, pACC119-17-2 and pACC127-17-0.9, it was suggested that these clones did not cover the 5' end of the ACC gene.

EXAMPLE 9

Cloning of the Franking Region of the Insert Fragment in pACC127-17-0.9 from the Genome of *P. rhodozyma* by Genome Walking Method PCR primer acc26 (SEQ ID NO:8) was synthesized based on the internal sequence of pACC127-17-0.9 and used for genome walking method.

In the PCR reaction using acc26 primer, a 2.6 kb PCR band emerged from the genomic PvuII library. This PCR band was cloned into pCR2.1-TOPO (Invitrogen) and it was revealed that this clone contained 5' fragment of ACC gene as a result of BLAST X analysis. This clone was named as pACCPvu126 and used for further study.

EXAMPLE 10

Southern Blot Hybridization by using pACCPvu126 as a Probe

Southern blot hybridization was performed to clone a genomic fragment which covered 5' end of ACC gene from *P. rhodozyma*. In a similar manner as Example 7, Southern blot hybridization was performed. A probe was prepared by labeling a template DNA (EcoRI-digested pACCPvu116) with DIG multipriming method (Boehringer Mannheim). Hybridization was performed with the method specified by the manufacturer. As a result, a hybridized band whose size was close to 5.0 kb was visualized.

EXAMPLE 11

Cloning of the Genomic Clone Covering 5' End of ACC Gene

In a similar manner to Example 8, the genomic fragment containing the insert fragment in pACCPvu126 was cloned by plaque hybridization. The genomic library covering 2.7 to 6.0 kb in length prepared in Example 8 was also used. Twelve positive plaques which hybridized to the insert fragment of pACCPvu126 labeled with DIG were isolated and subjected to in vivo excision to obtain plasmid DNA. As a result of sequencing for thus isolated plasmids, most of the plasmids had the identical sequence to the insert fragment of pACCPvu126. One of the clones was named as pACC204 and used for further study.

EXAMPLE 12

Cloning of the Gapped Region Between pACC204 and pACC127-17-0.9

As a result of BLAST X analysis against known acetyl-CoA carboxylase genes succeeding to the sequencing study of 3' end of the insert fragment in pACC204 and 5' end of the insert fragment in pACC127-17-0.9, it was suggested that an approximately 0.3 kb fragment could be still missing for a coverage of the entire ACC gene. The following PCR primers were synthesized based on the internal sequence of pACC204 and pACC127-17-0.9: acc43 (sense primer) (SEQ ID NO:9) and acc44 (antisense primer) (SEQ ID NO:10). After the PCR reaction of 25 cycles of 94° C. for 15 seconds, 55° C. for 30 seconds and 72° C. for 15 seconds by using HF polymerase (Clontech) as a DNA polymerase and a genomic DNA obtained in Example 3 as a template, the reaction mixture was applied to agarose gel electrophoresis. One PCR band that had a desired length (0.3 kb) was recovered from the agarose gel and purified by QIAquick (QIAGEN) according to the method by the manufacturer and then cloned into pCR2.1-TOPO (Invitrogen). After transformation of competent *E. coli* TOP 10, 6 white colonies were selected and plasmids were isolated with Automatic DNA isolation system. As a result of sequencing, it was found that 5 clones had an identical sequence from each other. One of the isolated clones was designated as pACC210.

EXAMPLE 13

Sequencing of a Complete Genomic Fragment Containing ACC Gene pACC204, pACC210, pACC127-17-0.9, pACC119-17-2, pACC119-17-0.6, pACC1224 and pACC119-18 were sequenced with primer walking procedure by using Auto-Read sequencing kit (Pharmacia).

As a result of sequencing, the nucleotide sequence comprising 10561 base pairs of the genomic fragment containing the ACC gene from *P. rhodozyma* containing its promoter (1445 base pairs) and terminator (1030 base pairs) was determined (SEQ ID NO:1).

The coding region was 8086 base pairs long and consisted of 19 exons and 18 introns. Introns were dispersed all through the coding region without 5' or 3' bias. It was found that an open reading frame (SEQ ID NO:2) consists of 2187 amino acids (SEQ ID NO:3) whose sequence is strikingly similar to the known amino acid sequence of acetyl-CoA carboxylase from other species (56.28% identity to acetyl-CoA carboxylase from *Emericella nidulans*) as a result of homology search by GENETYX-SV/RC software (Software Development Co., Ltd., Tokyo, Japan).

FIG. 1 depicts a cloned DNA fragment covering ACC gene region on the chromosome of *P. rhodozyma*.

EXAMPLE 14

Construction of Antisense Plasmid for ACC Gene

An antisense gene fragment which covers the entire structure gene for ACC gene is amplified by PCR and then cloned into an integration vector in which the antisense ACC gene is transcribed by its own ACC promoter in *P. rhodozyma*.

The primers include an asymmetrical recognition sequence for the restriction enzyme, SfiI (GGCCNNNNNGGCC) but their asymmetrical hang-over sequence is designed to be different. This enables a directional cloning into expression vector which has the same asymmetrical sequence at their ligation sequence. The use of such a construction is disclosed in EP 1,158,051.

For the promoter and terminator fragment which can drive the transcription of the antisense ACC gene, the ACC promoter and terminator is cloned from the chromosome by using the sequence information listed in SEQ ID NO:1. The ACC terminator fragment is fused to a G418 resistant cassette by ligating the DNA fragment containing the ACC terminator to a G418 resistant cassette of pG418Sa330 (EP 1,035,206) to an appropriate vector such as pBluescriptII KS- (Stratagene).

Then, 3.1 kb of the SacI fragment containing ribosomal DNA (rDNA) locus (Wery et al., Gene, 184, 89-97, 1997) is inserted downstream of the G418 cassette on thus prepared plasmid. The rDNA fragment exists in multicopies on the chromosome of eukaryote. The integration event via the rDNA fragment would result in multicopied integration onto the chromosome of the host used and this enables the overexpression of foreign genes which are harbored in expression vector.

Subsequently, ACC promoter is inserted in the upstream of ACC terminator to construct of expression vector which functions in *P. rhodozyma*.

Finally, the antisense ACC construct is completed by inserting the 1.5 kb of SfiI fragment containing antisense ACC into thus prepared expression vector functioning in *P. rhodozyma*. A similar plasmid construction is disclosed in EP 1,158,051.

EXAMPLE 15

Transformation of *P. rhodozyma* with an ACC-Antisense Vector

The ACC-antisense vector thus prepared is transformed into *P. rhodozyma* wild type strain, ATCC96594. The protocol for the biolistic transformation is disclosed in EP 1,158,051.

EXAMPLE 16

Characterization of Antisense ACC Recombinant of *P. rhodozyma*

Antisense ACC recombinant of *P. rhodozyma*, ATCC96594 is cultured in 50 ml of YPD medium in 500 ml Erlenmeyer flask at 20° C. for 3 days by using their seed culture which grows in 10 ml of YPD medium in test tubes (21 mm in diameter) at 20° C. for 3 days. For analysis of carotenoid produced appropriate volume of culture broth is withdrawn and used for analysis of their growth, productivity of carotenoids, especially astaxanthin. For analysis of growth, optical density at 660 nm is measured by using a UV-1200 photometer (Shimadzu Corp., Kyoto, Japan) in addition to the determination of their dried cell mass by drying up the cells derived from 1 ml of broth after microcentrifugation at 100° C. for one day. For the analysis of the content of astaxanthin and total carotenoids, cells are harvested from 1.0 ml of broth after microcentrifugation and used for the extraction of the carotenoids from cells of *P. rhodozyma* by disruption with glass beads. After extraction, disrupted cells are removed by centrifugation and the resultant is analyzed for carotenoid content with HPLC. The HPLC condition used is as follows: HPLC column: Chrompack Lichrosorb si-60 (4.6 mm, 250 mm), Temperature: room temperature, Eluent: acetone/hexane (18/82) add 1 ml/L of water to eluent, Injection volume: 10 µl, Flow rate: 2.0 ml/min, Detection: UV at 450 nm. A reference sample of astaxanthin can be obtained from Hoffmann La-Roche (Basel, Switzerland).

FIG. 1 depicts a deducted biosynthetic pathway from acetyl-CoA to astaxanthin in *P. rhodozyma*.

FIG. 2 depicts a cloned DNA fragment covering ACC gene region on the chromosome of *P. rhodozyma*.

The invention claimed is:

1. An isolated polynucleotide isolated from a microorganism comprising a nucleic acid molecule selected from the group consisting of:
   (a) nucleic acid molecules encoding the polypeptide depicted in SEQ ID NO:3;
   (b) nucleic acid molecules comprising the coding sequence as depicted in SEQ ID NO:2;
   (c) nucleic acid molecules encoding a polypeptide whose sequence has an identity of 99% or more to the amino acid sequence of the polypeptide encoded by a nucleic acid molecule of (a) or (b) having acetyl-CoA carboxylase activity; and
   (d) nucleic acid molecules encoding a polypeptide derived from the polypeptide whose sequence has an identity of 95% or more to the amino acid sequence of the polypeptide encoded by a nucleic acid molecule of (a) or (b) having acetyl-CoA carboxylase activity, wherein said nucleic acid is isolated from Phaffia.

2. The isolated polynucleotide of claim 1, wherein said polynucleotide encodes the amino acid sequence of SEQ ID NO:3 or has identity of 99% or more with SEQ ID NO:3.

3. The isolated-polynucleotide of claim 1 wherein said polynucleotide is isolated from a strain of *P. rhodozyma* or *Xanthophyllomyces dendrorhous*.

4. A method for making a recombinant vector comprising inserting the polynucleotide of claim 1 into a vector.

5. A recombinant vector comprising the polynucleotide of claim 1.

6. The vector of claim 5 in which the polynucleotide of claim 1 is operatively linked to expression control sequences allowing expression in prokaryotic or eukaryotic cells.

7. A method of making a recombinant microorganism comprising introducing the vector of claim 5 into said microorganism.

8. The method of claim 7, wherein said microorganism is selected from *E. coli* or *S. cerevisiae*.

9. A recombinant microorganism containing the vector of claim 5.

10. A process for producing a polypeptide having acetyl-CoA carboxylase activity comprising culturing the recombinant microorganism of claim 9 and recovering the polypeptide from the culture of said recombinant microorganism.

11. An isolated polynucleotide sequence that comprises the sequence set forth in SEQ ID NO:2.

12. An isolated polynucleotide sequence that consists of the sequence set forth in SEQ ID NO:2.

13. An isolated polynucleotide sequence that encodes the polypeptide sequence set forth in SEQ ID NO:3.

14. An isolated polynucleotide sequence from Phaffia that hybridizes under high stringency conditions to SEQ ID NO:2 or its complement and encodes a polypeptide that has acetyl-CoA carboxylase activity, wherein the high stringency conditions include hybridizing in 6×SSC, 0.5% SDS, 100 μg/ml denatured salmon sperm DNA, 50% formamide overnight at 42° C. and washing once in 2×SSC, 0.5% SDS at room temperature for 15 minutes followed by a second wash in 0.1×SSC, 0.5% SDS at room temperature for 15 minutes.

15. An isolated polynucleotide sequence that encodes a polypeptide sequence that is at least 99% identical to the polypeptide sequence set forth in SEQ ID NO:3 and has acetyl-CoA carboxylase activity.

16. A recombinant vector comprising a polynucleotide according to any of claims 11, 12, 13, 14, or 15.

\* \* \* \* \*

SEQUENCE LISTING

<160> NUMBER OF SEQ ID NOS: 10

<210> SEQ ID NO 1
<211> LENGTH: 10561
<212> TYPE: DNA
<213> ORGANISM: Phaffia rhodozyma
<220> FEATURE:
<221> NAME/KEY: 5'UTR

```
<222> LOCATION: (1221)..(1222)
<220> FEATURE:
<221> NAME/KEY: exon
<222> LOCATION: (1446)..(1482)
<220> FEATURE:
<221> NAME/KEY: Intron
<222> LOCATION: (1483)..(1675)
<220> FEATURE:
<221> NAME/KEY: exon
<222> LOCATION: (1676)..(1758)
<220> FEATURE:
<221> NAME/KEY: Intron
<222> LOCATION: (1759)..(1832)
<220> FEATURE:
<221> NAME/KEY: exon
<222> LOCATION: (1833)..(1957)
<220> FEATURE:
<221> NAME/KEY: Intron
<222> LOCATION: (1958)..(2030)
<220> FEATURE:
<221> NAME/KEY: exon
<222> LOCATION: (2031)..(2171)
<220> FEATURE:
<221> NAME/KEY: Intron
<222> LOCATION: (2172)..(2243)
<220> FEATURE:
<221> NAME/KEY: exon
<222> LOCATION: (2244)..(2641)
<220> FEATURE:
<221> NAME/KEY: Intron
<222> LOCATION: (2642)..(2745)
<220> FEATURE:
<221> NAME/KEY: exon
<222> LOCATION: (2746)..(2991)
<220> FEATURE:
<221> NAME/KEY: Intron
<222> LOCATION: (2992)..(3074)
<220> FEATURE:
<221> NAME/KEY: exon
<222> LOCATION: (3075)..(3443)
<220> FEATURE:
<221> NAME/KEY: Intron
<222> LOCATION: (3444)..(3517)
<220> FEATURE:
<221> NAME/KEY: exon
<222> LOCATION: (3518)..(3552)
<220> FEATURE:
<221> NAME/KEY: Intron
<222> LOCATION: (3553)..(3625)
<220> FEATURE:
<221> NAME/KEY: exon
<222> LOCATION: (3626)..(3750)
<220> FEATURE:
<221> NAME/KEY: Intron
<222> LOCATION: (3751)..(3827)
<220> FEATURE:
<221> NAME/KEY: exon
<222> LOCATION: (3828)..(4026)
<220> FEATURE:
<221> NAME/KEY: Intron
<222> LOCATION: (4027)..(4095)
<220> FEATURE:
<221> NAME/KEY: exon
<222> LOCATION: (4096)..(4911)
<220> FEATURE:
<221> NAME/KEY: Intron
<222> LOCATION: (4912)..(4983)
<220> FEATURE:
<221> NAME/KEY: exon
<222> LOCATION: (4984)..(5384)
<220> FEATURE:
<221> NAME/KEY: Intron
<222> LOCATION: (5385)..(5455)
<220> FEATURE:
<221> NAME/KEY: exon
<222> LOCATION: (5456)..(5608)
<220> FEATURE:
<221> NAME/KEY: Intron
<222> LOCATION: (5609)..(5673)
```

```
-continued

<220> FEATURE:
<221> NAME/KEY: exon
<222> LOCATION: (5674)..(5805)
<220> FEATURE:
<221> NAME/KEY: Intron
<222> LOCATION: (5806)..(5870)
<220> FEATURE:
<221> NAME/KEY: exon
<222> LOCATION: (5871)..(6832)
<220> FEATURE:
<221> NAME/KEY: Intron
<222> LOCATION: (6833)..(6898)
<220> FEATURE:
<221> NAME/KEY: exon
<222> LOCATION: (6899)..(6976)
<220> FEATURE:
<221> NAME/KEY: Intron
<222> LOCATION: (6977)..(7047)
<220> FEATURE:
<221> NAME/KEY: exon
<222> LOCATION: (7048)..(7227)
<220> FEATURE:
<221> NAME/KEY: Intron
<222> LOCATION: (7228)..(7295)
<220> FEATURE:
<221> NAME/KEY: exon
<222> LOCATION: (7296)..(9160)
<220> FEATURE:
<221> NAME/KEY: Intron
<222> LOCATION: (9161)..(9230)
<220> FEATURE:
<221> NAME/KEY: exon
<222> LOCATION: (9231)..(9530)
<220> FEATURE:
<221> NAME/KEY: polyA_site
<222> LOCATION: (9813)..(9814)

<400> SEQUENCE: 1
caacagacag acaaaggaac ttacgtgtac atactggtct ttccaatgtc gcggcgtcga      60
gattaactag aacaatactt gacaatcgaa tctcttattc tgccctagtt gaaggcgtct     120
gttcaaattg atcaagatct tccaatcatt gacatccagg tattcgcatt cgactctgct     180
cgtatgtact gttccgattt tcttatggcc accagatttc aactctgata tacattggtt     240
caccctgtct ttgtctcttt gcctttcgtt ccatctagcg ctgttcaacg gatcactcag     300
tcggcttgac tcaactccct ctggaacgtg tgccttatct caggttctga tttctcctca     360
gccagtatgc gcacaaagca gcgatcgtga cttttttgctc cataagacct ctcagcgggg     420
aatatatgac actcatacat cgatagctcg tatgtttttct ttgatcactt cctaaaatgt     480
aacggcaact gacattcaac atgatgcgct ttcatagatc aactacttcc gactacgatg     540
accgttcttc tatacagccc agtcagctcg tcgacctcac ataaagtgac tgagaccgcg     600
atctcgaaca tcttattcct tccaccgtta gctgagaagt ggattacacc atcaatagaa     660
tcatctaccc cgttcttgcc tggactaatg cgtcaggagc tcttggataa aggagaaata     720
gctgagcaga ccatcacctt ggatgatgtc cgtctgtggc tgaactccgg aggtcgagtg     780
gcgtgctgca acgcacttcg aggaatttgg gaagtgaacc tcgtttggag tgataaatga     840
gattacgaaa gtctgttcga acatccatg cttcatgata accgataacg cttaaatctt     900
gagagtgcgc acatcgatcg cctttttatat atggggttgg ggaaacataa agtgttcata     960
gactattgtt catatatctt aaagtacaaa gacgcatcta accctaagcc tgaatgattg    1020
gcaaaatcct agtaagaccg tgaaattccg aagaatacgc agttcattaa taagatatat    1080
gcttaggtaa gcagcggttg ctcccccaac caacctcatc cgaaattccc caggggggttg    1140
agattctcaa ggctttgaat ccccatcccg tcaagttggt cttaaaccct tcatctctac    1200
```

-continued

```
ttgttacttc ttttcttctt gacctccttc ccccactccc tcctattctc tgaacgaact    1260
cgcctccctg tccatctact cttcttcggt tttcttttgg gttttttactt ttctcgttcc    1320 tcctccatct tttccatctct tttcgtatct gtgggtaact ttgcatccaa gggccctcac   1380
acataaccct atatccatct tcctccattc acacacatct gtactcaacc aacaaagctc    1440 acaag atg gtt gtc gat cac gag agc gta agg cat ttc atc g              1482
      Met Val Val Asp His Glu Ser Val Arg His Phe Ile
       1               5                  10 gtaagcgttc ttgttctttt ccttgtctgg ctccctgcat tttcttaaac gatctaggaa    1542
gagagggaaa ttacatctgg tcaatttttcc gcgctctttt ccttggggac aaaagaatgc   1602
ctttctgtga tcggagatcg gttgctgatc tcttttgtct tgttcttttt gctctttccc    1662 tccccttac cag gt  gga aac gca ctt gag aac gcc cct ccg tca agc        1710
              Gly Gly Asn Ala Leu Glu Asn Ala Pro Pro Ser Ser
                      15                  20 gtc acc gat ttc gtt aga agt caa gat ggt cac acg gtc atc acc aaa     1758
Val Thr Asp Phe Val Arg Ser Gln Asp Gly His Thr Val Ile Thr Lys
25                  30                  35                  40 gtcagtaatt tcatttttt ccttcacgta gcctcagggc caaggagcta aattgcttct    1818
gtatcatttc tcag gtc ctc att gcc aac aac gga atc gct gct gta aaa    1868
              Val Leu Ile Ala Asn Asn Gly Ile Ala Ala Val Lys
                                45                  50 gag atc cga tca gtt cgt aaa tgg gct tac gag acg ttt gga gat gag    1916
Glu Ile Arg Ser Val Arg Lys Trp Ala Tyr Glu Thr Phe Gly Asp Glu
55                  60                  65 cga gcc atc gaa ttt acg gta atg gcc act cca gaa gat tt              1957
Arg Ala Ile Glu Phe Thr Val Met Ala Thr Pro Glu Asp Leu
       70                  75                  80 gttcgtacca atcacataag ctttccttga gtcagggaca tcctctaatt aattcaactt    2017
gagcgccata cag g aag gtg aac tgc gac tat att cga atg gct gat cga    2067
              Lys Val Asn Cys Asp Tyr Ile Arg Met Ala Asp Arg
                              85                  90 gtc gtc gaa gtt cct gga gga act aac aac aac aat cac tct aac gtc    2115
Val Val Glu Val Pro Gly Gly Thr Asn Asn Asn Asn His Ser Asn Val
95                  100                 105                 110 gac ctc atc gtt gac att gcc gag cga ttc aat ata cat gct gtt tgg    2163
Asp Leu Ile Val Asp Ile Ala Glu Arg Phe Asn Ile His Ala Val Trp
               115                 120                 125 gct gga tg  gtaagtaaaa taggacctta acatgttgga agaagagtgt              2211
Ala Gly Trp ccacttaaac gcgctttctt tccatccgac ag g ggt cac gct tcg gaa aac ccc   2265
                                    Gly His Ala Ser Glu Asn Pro
                                      130                 135 aga ctt ccc gag tct ctc gcc gcc tca aag aac aag atc gtc ttc att    2313
Arg Leu Pro Glu Ser Leu Ala Ala Ser Lys Asn Lys Ile Val Phe Ile
         140                 145                 150 ggt cct ccc gga tcc gct atg cga tcc ctt gga gac aag att tct tcg    2361
Gly Pro Pro Gly Ser Ala Met Arg Ser Leu Gly Asp Lys Ile Ser Ser
         155                 160                 165 acc atc gtt gcc cag tct gcc cag gtg ccg tgt atg gcc tgg tct gga    2409
Thr Ile Val Ala Gln Ser Ala Gln Val Pro Cys Met Ala Trp Ser Gly
170                 175                 180 tca ggc atc act gat aca gag ctc agc cct cag ggc ttc gtg act gtg    2457
Ser Gly Ile Thr Asp Thr Glu Leu Ser Pro Gln Gly Phe Val Thr Val
185                 190                 195                 200 ccc gat ggg cca tat cag gct gct tgt gta aag acg gtg gag gat ggt    2505
```

```
                                       -continued

Pro Asp Gly Pro Tyr Gln Ala Ala Cys Val Lys Thr Val Glu Asp Gly
                     205                 210                 215 ttg gtg cga gcc gag aag atc ggt ttg cca gtt atg atc aag gcc tct      2553
Leu Val Arg Ala Glu Lys Ile Gly Leu Pro Val Met Ile Lys Ala Ser
                220                 225                 230 gag gga gga gga gga aag ggt atc cga atg gtt cac agc atg gac aca      2601
Glu Gly Gly Gly Gly Lys Gly Ile Arg Met Val His Ser Met Asp Thr
            235                 240                 245 ttc aag aac tcc tac aac tcc gtc gct tcc gag gtg cca g gtaagttcac     2651
Phe Lys Asn Ser Tyr Asn Ser Val Ala Ser Glu Val Pro
        250                 255                 260 tctgtttgac tggagatttg agcacaatct ctaccatggg agttcaagaa ggaatacccca   2711 ctcatgaatt gacgactgcg ttcttgacct ctag ga tct ccg att ttc atc atg    2765
                                       Gly Ser Pro Ile Phe Ile Met

265 gcc ttg gct gga tct gct cga cat ttg gag gtc cag ctc ctt gct gat      2813
Ala Leu Ala Gly Ser Ala Arg His Leu Glu Val Gln Leu Leu Ala Asp
        270                 275                 280 cag tac gga aac gct atc tct ttg ttc ggt cga gat tgc tct gtt cag      2861
Gln Tyr Gly Asn Ala Ile Ser Leu Phe Gly Arg Asp Cys Ser Val Gln
285                 290                 295                 300 cga cga cat cag aag atc att gag gag gct ccc gtc acg atc gct cgt      2909
Arg Arg His Gln Lys Ile Ile Glu Glu Ala Pro Val Thr Ile Ala Arg
                305                 310                 315 cca gag aga ttc gaa gag atg gag aag gct gct gtc agg ttg gcc aag      2957
Pro Glu Arg Phe Glu Glu Met Glu Lys Ala Ala Val Arg Leu Ala Lys
                320                 325                 330 tta gta gga tat gtt agt gcc ggt acc gtc gaa t gtaaggaaca             3001
Leu Val Gly Tyr Val Ser Ala Gly Thr Val Glu
            335                 340 aacagctacc tctcattctg tttttcgag atagtcaact acatcactt ttctttgcc      3061 ggatttctct tag ac ctc tac tct cac gcc gac gac tca ttc ttc ttc        3109
                Tyr Leu Tyr Ser His Ala Asp Asp Ser Phe Phe Phe
                    345                 350                 355 ctc gaa ctc aac cct cga ctt caa gtc gag cac cct act acc gag atg      3157
Leu Glu Leu Asn Pro Arg Leu Gln Val Glu His Pro Thr Thr Glu Met
                360                 365                 370 gtc tcg ggt gtc aac ctt ccc gct gct cag ctt cag att gct atg ggt      3205
Val Ser Gly Val Asn Leu Pro Ala Ala Gln Leu Gln Ile Ala Met Gly
                375                 380                 385 atc cct ctt tct cga att cgg gat att cga gtc ctc tac ggt ctc gat      3253
Ile Pro Leu Ser Arg Ile Arg Asp Ile Arg Val Leu Tyr Gly Leu Asp
            390                 395                 400 ccc cac act gtt tcc gag atc gac ttc gac agc agc aga gcg gag tct      3301
Pro His Thr Val Ser Glu Ile Asp Phe Asp Ser Ser Arg Ala Glu Ser
405                 410                 415 gtc cag act cag agg aag cct agg ccc aag ggt cac gtc att gcc tgt      3349
Val Gln Thr Gln Arg Lys Pro Arg Pro Lys Gly His Val Ile Ala Cys
420                 425                 430                 435 cga atc acg agt gaa aac ccc gat gag ggg ttc aag ccg tct gcc gga      3397
Arg Ile Thr Ser Glu Asn Pro Asp Glu Gly Phe Lys Pro Ser Ala Gly
                440                 445                 450 gat atc caa gag ttg aac ttc aga agt aat act aac gtc tgg gga t        3443
Asp Ile Gln Glu Leu Asn Phe Arg Ser Asn Thr Asn Val Trp Gly
            455                 460                 465 gtgagtacag aggcttctca aagattctta tgtggaacaa atctctgact cttaaattgt   3503
gtttgacttt caag ac ttc tct gtt gga gct act gga gga att cat agt      3552
```

```
                    Tyr Phe Ser Val Gly Ala Thr Gly Gly Ile His Ser
                                470                 475 gtaagtttct tcgccaacaa tataatcaca ctagatccct atctaatctg aactggctta          3612
tctcttgtta tag ttc gcc gat tct caa ttc ggt cac gtg ttt gct tat            3661
            Phe Ala Asp Ser Gln Phe Gly His Val Phe Ala Tyr
                480                 485                 490 ggc tcc gac cga acg act gcc aga aag aat atg gtt atc gcc ttg aaa           3709
Gly Ser Asp Arg Thr Thr Ala Arg Lys Asn Met Val Ile Ala Leu Lys
            495                 500                 505 gag ctt tcc att cga gga gac ttc cga acc act gtc gag ta                    3750
Glu Leu Ser Ile Arg Gly Asp Phe Arg Thr Thr Val Glu Tyr
        510                 515                 520 gtgcgtatag cctggtacat ctcctttcaa tcacttacga tgaactgacc gatctgtctc         3810
gatcacgttt aatctag t ctt atc act ctt ctt gag acg agc gat ttc gag          3861
                     Leu Ile Thr Leu Leu Glu Thr Ser Asp Phe Glu
                                     525                 530 cag aac gcc att acc acc gct tgg ttg gat ggg ttg atc act aac aag           3909
Gln Asn Ala Ile Thr Thr Ala Trp Leu Asp Gly Leu Ile Thr Asn Lys
            535                 540                 545 ctt aca tct gag agg cct gat cca tca ctg gcc gtt att tgt ggt gca           3957
Leu Thr Ser Glu Arg Pro Asp Pro Ser Leu Ala Val Ile Cys Gly Ala
        550                 555                 560 att gtg aaa gct cac gtg gct tct gag aac tgt tgg gcc gaa tac cga           4005
Ile Val Lys Ala His Val Ala Ser Glu Asn Cys Trp Ala Glu Tyr Arg
565                 570                 575 cga gta ttg gac aag gga cag gtaagctctg tttctcatga agttttgac               4056
Arg Val Leu Asp Lys Gly Gln
580             585 tgaggcactc accactccgt acatgtttcc tgtttttag gtt ccc tcc aag gac            4110
                                         Val Pro Ser Lys Asp
                                                     590 act ctc aag aca gtg ttc act ctt gat ttc atc tat gag ggt gtt cgg           4158
Thr Leu Lys Thr Val Phe Thr Leu Asp Phe Ile Tyr Glu Gly Val Arg
            595                 600                 605 tac aat ttc acc gct gct cga gcc tcc ctc aac act tac cga ttg tat           4206
Tyr Asn Phe Thr Ala Ala Arg Ala Ser Leu Asn Thr Tyr Arg Leu Tyr
        610                 615                 620 cta aac gga gga aag acc gtg gtg tcc atc cga cct ttg gcc gat ggt           4254
Leu Asn Gly Gly Lys Thr Val Val Ser Ile Arg Pro Leu Ala Asp Gly
625                 630                 635 gga atg ctc gtt ctt ctc gat ggc cga tcc cac act ctc tac tgg agg           4302
Gly Met Leu Val Leu Leu Asp Gly Arg Ser His Thr Leu Tyr Trp Arg
640                 645                 650                 655 gag gaa gtc ggt acc ctc cga att cag gta gac gca aag act tgc ctg           4350
Glu Glu Val Gly Thr Leu Arg Ile Gln Val Asp Ala Lys Thr Cys Leu
                660                 665                 670 att gag cag gag aac gac ccc act cag ctc cga tca ccc tcg cct gga           4398
Ile Glu Gln Glu Asn Asp Pro Thr Gln Leu Arg Ser Pro Ser Pro Gly
            675                 680                 685 aag atc atc cgg ttt ttg gtc gaa agc gga gat cac atc tcc tcc gga           4446
Lys Ile Ile Arg Phe Leu Val Glu Ser Gly Asp His Ile Ser Ser Gly
        690                 695                 700 gat atc tat gct gag gtt gag gtc atg aag atg atc ttg ccc ttg att           4494
Asp Ile Tyr Ala Glu Val Glu Val Met Lys Met Ile Leu Pro Leu Ile
705                 710                 715 gcc cag gag tcc ggt cac gtt cag ttt gtc aag caa gcc ggt gtg acc           4542
Ala Gln Glu Ser Gly His Val Gln Phe Val Lys Gln Ala Gly Val Thr
720                 725                 730                 735
```

```
                                                                -continued gtc gat cct gga gcg att att ggg atc ttg agt ctt gat gac cct acg       4590
Val Asp Pro Gly Ala Ile Ile Gly Ile Leu Ser Leu Asp Asp Pro Thr
            740                 745                 750 cga gtg aag aag gcg aag ccc ttc gag ggt ctc ctg cct gtg act ggt       4638
Arg Val Lys Lys Ala Lys Pro Phe Glu Gly Leu Leu Pro Val Thr Gly
            755                 760                 765 ctc cct aac ctg ccc ggt aac aga cct cac cag cgg cta cag ttc cag       4686
Leu Pro Asn Leu Pro Gly Asn Arg Pro His Gln Arg Leu Gln Phe Gln
            770                 775                 780 ctt gag tcg ata tac tcg gtc ttg gat gga tac gag agt gac tcc act       4734
Leu Glu Ser Ile Tyr Ser Val Leu Asp Gly Tyr Glu Ser Asp Ser Thr
            785                 790                 795 gca aca atc ctc cga tca ttc tct gaa aac ctt tat gat cct gat ctt       4782
Ala Thr Ile Leu Arg Ser Phe Ser Glu Asn Leu Tyr Asp Pro Asp Leu
800                 805                 810                 815 gct ttc gga gag gct tta tcc atc att tcc gtc ctt tct ggg aga atg       4830
Ala Phe Gly Glu Ala Leu Ser Ile Ile Ser Val Leu Ser Gly Arg Met
                820                 825                 830 cct gcc gat ctt gag gag agc att cga gag gtc atc agc gaa gct cag       4878
Pro Ala Asp Leu Glu Glu Ser Ile Arg Glu Val Ile Ser Glu Ala Gln
                835                 840                 845 tcg aag cct cac gcc gag ttc cct gga tca aag gtgtgtagtt gatcgcagag    4931
Ser Lys Pro His Ala Glu Phe Pro Gly Ser Lys
            850                 855 ttatgactgt atacatcgac cagaagctta cccatctctt tcgtgtgcac ag atc ctc    4989
                                                          Ile Leu
                                                              860 aaa gtc gtc gag cgg tac atc gat aat ttg cga cct cag gag agg gct       5037
Lys Val Val Glu Arg Tyr Ile Asp Asn Leu Arg Pro Gln Glu Arg Ala
                    865                 870                 875 atg gtc cga act cag atc gaa ccc atc gtt ggt att gct gag aag aac       5085
Met Val Arg Thr Gln Ile Glu Pro Ile Val Gly Ile Ala Glu Lys Asn
                880                 885                 890 gtt ggc ggt cct aag ggt tac gcc tct tac gtc tta gct acc atc ctt       5133
Val Gly Gly Pro Lys Gly Tyr Ala Ser Tyr Val Leu Ala Thr Ile Leu
            895                 900                 905 caa aag ttc ttg gcc gtt gag gcc gtt ttt gct act ggt agt gaa gag       5181
Gln Lys Phe Leu Ala Val Glu Ala Val Phe Ala Thr Gly Ser Glu Glu
    910                 915                 920 gcc att gtt ctc caa ctt cga gat gaa aac cga gaa tct ttg aac gac       5229
Ala Ile Val Leu Gln Leu Arg Asp Glu Asn Arg Glu Ser Leu Asn Asp
925                 930                 935                 940 gtc ctt ggt ctc gtc ctg gct cac tcg cgt ctc agc gct cga tcc aag       5277
Val Leu Gly Leu Val Leu Ala His Ser Arg Leu Ser Ala Arg Ser Lys
                945                 950                 955 ctt gtt ctc tcc gtc ttt gat ctg atc aag tct atg cag ctc ctc aac       5325
Leu Val Leu Ser Val Phe Asp Leu Ile Lys Ser Met Gln Leu Leu Asn
                960                 965                 970 aac act gag ggt tct ttc ctt cat aag act atg aaa gcg ctt gcc gac       5373
Asn Thr Glu Gly Ser Phe Leu His Lys Thr Met Lys Ala Leu Ala Asp
                975                 980                 985 atg ccc acc aa  gtaggtttcc tcttgtagtt tacaaactat tgttgcgatg           5424
Met Pro Thr Lys
        990 tgttgacaaa gactctgttt ccgatctata g g gct cct ttg gcc agc aag gtg     5477
                                    Ala Pro Leu Ala Ser Lys Val
                                                        995 tct ttg aag gct cgg gaa  att ctt atc tct tgc  tct ctt ccc tct        5522
Ser Leu Lys Ala Arg Glu  Ile Leu Ile Ser Cys  Ser Leu Pro Ser
1000                    1005                 1010
```

-continued

| | | |
|---|---|---|
| tac gag gag agg ttg ttc cag atg gaa aag atc ctt aac tct tct<br>Tyr Glu Glu Arg Leu Phe Gln Met Glu Lys Ile Leu Asn Ser Ser<br>1015                       1020                      1025 | | 5567 |
| gtc acc act tct tac tac gga gag act gga ggt gga cac ag<br>Val Thr Thr Ser Tyr Tyr Gly Glu Thr Gly Gly Gly His Arg<br>1030                       1035                      1040 | | 5608 |
| gtttgtcctc tcccatgtgt ttctagttca tagctctctg ctgactctga tccgattttc | | 5668 |
| aacag a aac cct tcg gtt gat gtt ctg act gag atc tca aac tct<br>        Asn Pro Ser Val Asp Val Leu Thr Glu Ile Ser Asn Ser<br>            1045                      1050                      1055 | | 5713 |
| cga ttc acc gtc tac gat gtc ctg tcc tcc ttc ttc aag cac gat<br>Arg Phe Thr Val Tyr Asp Val Leu Ser Ser Phe Phe Lys His Asp<br>             1060                     1065                     1070 | | 5758 |
| gat cct tgg att gtt ctt gct agt ttg acc gtc tac gtt ctt cga<br>Asp Pro Trp Ile Val Leu Ala Ser Leu Thr Val Tyr Val Leu Arg<br>             1075                     1080                     1085 | | 5803 |
| gc gtaagtgatc gttcttctcc tcttgcccaa acaatgactg acagttctat<br>Ala | | 5855 |
| ctattccatc tgcag t tac cga gag tac agt att ctt gat atg caa cat<br>                    Tyr Arg Glu Tyr Ser Ile Leu Asp Met Gln His<br>                            1090                     1095 | | 5904 |
| gag caa ggt cag gat ggc gct gct gga gtc atc act tgg cga ttc<br>Glu Gln Gly Gln Asp Gly Ala Ala Gly Val Ile Thr Trp Arg Phe<br>        1100                     1105                     1110 | | 5949 |
| aag ctc aac cag ccc atc gct gag tct tct act ccc cga gtt gac<br>Lys Leu Asn Gln Pro Ile Ala Glu Ser Ser Thr Pro Arg Val Asp<br>      1115                     1120                     1125 | | 5994 |
| tcg aat cga gac gtt tac cga gtc ggt tcg ctt tct gat ttg acc<br>Ser Asn Arg Asp Val Tyr Arg Val Gly Ser Leu Ser Asp Leu Thr<br>        1130                     1135                     1140 | | 6039 |
| tac aag atc aag cag agt cag acc gag ccc ctc cga gct ggt gtc<br>Tyr Lys Ile Lys Gln Ser Gln Thr Glu Pro Leu Arg Ala Gly Val<br>      1145                     1150                     1155 | | 6084 |
| atg acg agc ttc aac aac ttg aag gag gtt cag gac gga ctc ttg<br>Met Thr Ser Phe Asn Asn Leu Lys Glu Val Gln Asp Gly Leu Leu<br>        1160                     1165                     1170 | | 6129 |
| aat gtt ctg tct ttc ttc cct gct tac cat cat caa gat ttc act<br>Asn Val Leu Ser Phe Phe Pro Ala Tyr His His Gln Asp Phe Thr<br>      1175                     1180                     1185 | | 6174 |
| caa cga cat ggt cag gac agt gcc atg ccc aac gtt ctc aac att<br>Gln Arg His Gly Gln Asp Ser Ala Met Pro Asn Val Leu Asn Ile<br>        1190                     1195                     1200 | | 6219 |
| gct atc cgg gct ttc gag gag aag gac gac atg tct gat ctt gat<br>Ala Ile Arg Ala Phe Glu Glu Lys Asp Asp Met Ser Asp Leu Asp<br>      1205                     1210                     1215 | | 6264 |
| tgg gcc aag agt gtt gag tcg ctg gta atg cag atg tct gcc gag<br>Trp Ala Lys Ser Val Glu Ser Leu Val Met Gln Met Ser Ala Glu<br>        1220                     1225                     1230 | | 6309 |
| atc cag aag aag gga att cga cga gtt acc ttc ttg gtt tgc cga<br>Ile Gln Lys Lys Gly Ile Arg Arg Val Thr Phe Leu Val Cys Arg<br>      1235                     1240                     1245 | | 6354 |
| aag ggc gtt tac ccc tcc tac ttc acc ttc aga caa gag ggt gcc<br>Lys Gly Val Tyr Pro Ser Tyr Phe Thr Phe Arg Gln Glu Gly Ala<br>        1250                     1255                     1260 | | 6399 |
| cag ggc ccc tgg aga gag gag gag aag att cga aac atc gag cct<br>Gln Gly Pro Trp Arg Glu Glu Glu Lys Ile Arg Asn Ile Glu Pro<br>      1265                     1270                     1275 | | 6444 |
| gct cta gcc agt cag ctt gag ctc aac cga ctc tcg aat ttc aag | | 6489 |

```
                                                   -continued

Ala Leu Ala Ser Gln Leu Glu  Leu Asn Arg Leu Ser  Asn Phe Lys
    1280            1285              1290 gtc acc cct atc ttc gta gac  aac aga cag atc cac  atc tac aag          6534
Val Thr Pro Ile Phe Val Asp  Asn Arg Gln Ile His  Ile Tyr Lys
    1295            1300              1305 gga gtg ggt aag gag aac tct  tcc gat gtt cga ttc  ttt atc cgg          6579
Gly Val Gly Lys Glu Asn Ser  Ser Asp Val Arg Phe  Phe Ile Arg
    1310            1315              1320 gct ttg gtt cga cct gga cgg  gtc cag gga tcg atg  aag gct gcc          6624
Ala Leu Val Arg Pro Gly Arg  Val Gln Gly Ser Met  Lys Ala Ala
    1325            1330              1335 gag tat ctc atc tcc gag tgc  gat cga ctg ctc act  gat atc ctg          6669
Glu Tyr Leu Ile Ser Glu Cys  Asp Arg Leu Leu Thr  Asp Ile Leu
    1340            1345              1350 gac gcc ttg gag gtt gtt gga  gcc gag act cga aac  gcc gat tgc          6714
Asp Ala Leu Glu Val Val Gly  Ala Glu Thr Arg Asn  Ala Asp Cys
    1355            1360              1365 aac cat gtt gga att aac ttc  atc tat aac gtt ctt  gtc gac ttc          6759
Asn His Val Gly Ile Asn Phe  Ile Tyr Asn Val Leu  Val Asp Phe
    1370            1375              1380 gac gac gtc cag gag gcc ctt  gcc ggg ttc att gag  agg cac gga          6804
Asp Asp Val Gln Glu Ala Leu  Ala Gly Phe Ile Glu  Arg His Gly
    1385            1390              1395 aag agg ctt tgg cga ctt cga  gtg acc g gtaagtgttc tctcggcatt          6852
Lys Arg Leu Trp Arg Leu Arg  Val Thr
    1400            1405 gaattcagca atgagctgtg actaacgggt ttcttcggta tattag ct  tct gaa         6906
                                                      Ala Ser Glu
                                                              1410 atc cga atg gtt ctt  gag gac gac gag ggt  aac gtc acc ccc atc          6951
Ile Arg Met Val Leu  Glu Asp Asp Glu Gly  Asn Val Thr Pro Ile
             1415                 1420              1425 cga tgc tgc att gag  aac gtt tct g gtaagcagtc caaaataact              6996
Arg Cys Cys Ile Glu  Asn Val Ser
             1430 gataatccta ttcagtctag acattgtaac tgatgcattt ctcgttctta g gt  ttc        7052
                                                            Gly Phe
                                                                1435 gtc gtg aag tac cac  gcc tac cag gag gtt  gag acc gag aag ggt          7097
Val Val Lys Tyr His  Ala Tyr Gln Glu Val  Glu Thr Glu Lys Gly
             1440                 1445              1450 act acc atc ttg aag  tca atc gga gac ctt  gga cct ctt cac ctt          7142
Thr Thr Ile Leu Lys  Ser Ile Gly Asp Leu  Gly Pro Leu His Leu
             1455                 1460              1465 cag cct gtc aac cat  gct tac cag acc aag  aac agt ctt cag ccc          7187
Gln Pro Val Asn His  Ala Tyr Gln Thr Lys  Asn Ser Leu Gln Pro
             1470                 1475              1480 cga cga tac cag gct  cac ttg gtt gga acg  act tac gtc t                7227
Arg Arg Tyr Gln Ala  His Leu Val Gly Thr  Thr Tyr Val
             1485                 1490 gttagtcaca tttcatgctc tggttttctg accgtcactg gttattgacg ttctgtttgg      7287 cgtcacag ac  gac tac ccc gat ctc ttc  gtt cag agt ttg cgc  aag         7333
             Tyr Asp Tyr Pro Asp Leu Phe  Val Gln Ser Leu Arg  Lys
                 1495            1500                1505 gtt tgg gct gag  gct gct gct aag att  cct cac ctc cgg gtg  cct         7378
Val Trp Ala Glu  Ala Ala Ala Lys Ile  Pro His Leu Arg Val  Pro
        1510                 1515                1520 agc gag cct ctt  acc gct acc gag ttg  gtt ctc gat gag aac  aac         7423
Ser Glu Pro Leu  Thr Ala Thr Glu Leu  Val Leu Asp Glu Asn  Asn
```

-continued

```
              1525                1530                1535
gag  ctt  cag  gag  gtc  gag  cga  cct  ccg  ggt  tcc  aac  tcg  tgt  ggt       7468
Glu  Leu  Gln  Glu  Val  Glu  Arg  Pro  Pro  Gly  Ser  Asn  Ser  Cys  Gly
                    1540                1545                1550 atg  gtc  gcc  tgg  atc  ttc  act  atg  ctc  act  ccc  gag  tat  ccc  aag       7513
Met  Val  Ala  Trp  Ile  Phe  Thr  Met  Leu  Thr  Pro  Glu  Tyr  Pro  Lys
               1555                1560                1565 ggt  cga  cga  gta  gtt  gcc  att  gcc  aac  gat  atc  acc  ttc  aag  att       7558
Gly  Arg  Arg  Val  Val  Ala  Ile  Ala  Asn  Asp  Ile  Thr  Phe  Lys  Ile
          1570                1575                1580 gga  tcc  ttt  ggt  cct  aag  gaa  gac  gat  tac  ttc  ttc  aag  gct  act       7603
Gly  Ser  Phe  Gly  Pro  Lys  Glu  Asp  Asp  Tyr  Phe  Phe  Lys  Ala  Thr
     1585                1590                1595 gaa  att  gcc  aag  aag  ctg  ggc  ctt  cct  cga  att  tac  ctc  tct  gcc       7648
Glu  Ile  Ala  Lys  Lys  Leu  Gly  Leu  Pro  Arg  Ile  Tyr  Leu  Ser  Ala
1600                1605                1610 aac  agt  gga  gct  aga  ctc  ggt  atc  gcg  gag  gag  ctc  ttg  cac  atc       7693
Asn  Ser  Gly  Ala  Arg  Leu  Gly  Ile  Ala  Glu  Glu  Leu  Leu  His  Ile
               1615                1620                1625 ttc  aag  gcg  gcc  ttc  gtt  gac  ccc  gca  aag  cct  tcc  atg  ggt  att       7738
Phe  Lys  Ala  Ala  Phe  Val  Asp  Pro  Ala  Lys  Pro  Ser  Met  Gly  Ile
          1630                1635                1640 aag  tat  cta  tac  ttg  acc  cct  gaa  act  tta  tcc  act  ctt  gcc  aag       7783
Lys  Tyr  Leu  Tyr  Leu  Thr  Pro  Glu  Thr  Leu  Ser  Thr  Leu  Ala  Lys
     1645                1650                1655 aag  gga  tcc  agc  gtc  acc  act  gag  gag  atc  gag  gat  gac  ggc  gag       7828
Lys  Gly  Ser  Ser  Val  Thr  Thr  Glu  Glu  Ile  Glu  Asp  Asp  Gly  Glu
1660                1665                1670 cga  cga  cac  aag  atc  acc  gcc  atc  atc  ggt  ctt  gca  gag  ggt  ttg       7873
Arg  Arg  His  Lys  Ile  Thr  Ala  Ile  Ile  Gly  Leu  Ala  Glu  Gly  Leu
               1675                1680                1685 gga  gtt  gag  tct  ctt  cga  gga  tcc  ggt  ctt  att  gct  gga  gcc  acc       7918
Gly  Val  Glu  Ser  Leu  Arg  Gly  Ser  Gly  Leu  Ile  Ala  Gly  Ala  Thr
          1690                1695                1700 act  cga  gct  tac  gag  gag  gga  atc  ttc  acc  atc  tct  ctc  gtt  act       7963
Thr  Arg  Ala  Tyr  Glu  Glu  Gly  Ile  Phe  Thr  Ile  Ser  Leu  Val  Thr
     1705                1710                1715 gcc  cga  tcg  gtc  ggt  atc  gga  gct  tac  ttg  gtt  cga  ttg  ggt  cag       8008
Ala  Arg  Ser  Val  Gly  Ile  Gly  Ala  Tyr  Leu  Val  Arg  Leu  Gly  Gln
1720                1725                1730 cga  gct  att  cag  gtt  gaa  ggc  aac  cct  atg  atc  ctt  act  gga  gct       8053
Arg  Ala  Ile  Gln  Val  Glu  Gly  Asn  Pro  Met  Ile  Leu  Thr  Gly  Ala
               1735                1740                1745 cag  tct  ctc  aac  aag  gtg  ctt  gga  cga  gag  gtt  tac  act  tcc  aac       8098
Gln  Ser  Leu  Asn  Lys  Val  Leu  Gly  Arg  Glu  Val  Tyr  Thr  Ser  Asn
          1750                1755                1760 ctt  cag  ctt  gga  gga  acc  cag  att  atg  gcc  cga  aac  ggt  acc  acg       8143
Leu  Gln  Leu  Gly  Gly  Thr  Gln  Ile  Met  Ala  Arg  Asn  Gly  Thr  Thr
     1765                1770                1775 cat  ctc  gtc  gct  gaa  tct  gat  ctc  gat  ggt  gct  ctc  aag  gtc  atc       8188
His  Leu  Val  Ala  Glu  Ser  Asp  Leu  Asp  Gly  Ala  Leu  Lys  Val  Ile
1780                1785                1790 cag  tgg  ctc  tcg  tat  gtg  ccc  gag  cga  aag  ggc  aag  gcc  att  cct       8233
Gln  Trp  Leu  Ser  Tyr  Val  Pro  Glu  Arg  Lys  Gly  Lys  Ala  Ile  Pro
               1795                1800                1805 atc  tgg  cct  tcc  gag  gac  cct  tgg  gac  cga  act  gtg  acc  tac  gag       8278
Ile  Trp  Pro  Ser  Glu  Asp  Pro  Trp  Asp  Arg  Thr  Val  Thr  Tyr  Glu
          1810                1815                1820 cct  ccc  cga  ggt  cct  tac  gat  cct  cga  tgg  ttg  ctt  gaa  gga  aag       8323
```

|  |  |  |  |  |  |  |  |  |
|---|---|---|---|---|---|---|---|---|
| Pro | Pro | Arg | Gly | Pro | Tyr | Asp | Pro | Arg | Trp | Leu | Leu | Glu | Gly | Lys |
|  |  | 1825 |  |  |  | 1830 |  |  |  |  | 1835 |

```
ccg gat gaa ggc ttg act ggt ctt ttc gac aag gga tct ttc atg       8368
Pro Asp Glu Gly Leu Thr Gly Leu Phe Asp Lys Gly Ser Phe Met
    1840            1845                    1850 gag acc ctt gga gat tgg gcc aag act atc gtc acc ggt cga gcc       8413
Glu Thr Leu Gly Asp Trp Ala Lys Thr Ile Val Thr Gly Arg Ala
1855                1860                1865 cga ctg gga ggc att cct atg ggt gtt att gct gtc gaa acc agg       8458
Arg Leu Gly Gly Ile Pro Met Gly Val Ile Ala Val Glu Thr Arg
        1870            1875                1880 acg acc gag aag atc atc gct gcc gat cct gcc aac cct gca gct       8503
Thr Thr Glu Lys Ile Ile Ala Ala Asp Pro Ala Asn Pro Ala Ala
            1885            1890                1895 ttc gag caa aag att atg gag gct ggt cag gtt tgg aac ccc aac       8548
Phe Glu Gln Lys Ile Met Glu Ala Gly Gln Val Trp Asn Pro Asn
                1900            1905                1910 gct gct tac aag acc gct caa tcc atc ttt gat atc aac aag gag       8593
Ala Ala Tyr Lys Thr Ala Gln Ser Ile Phe Asp Ile Asn Lys Glu
                    1915            1920                1925 ggt ctt cct ttg atg atc ctt gcc aac atc cga ggt ttc tct gga       8638
Gly Leu Pro Leu Met Ile Leu Ala Asn Ile Arg Gly Phe Ser Gly
        1930            1935                1940 gga cag ggt gat atg ttt gac gct atc ctc aag cag ggt tct aag       8683
Gly Gln Gly Asp Met Phe Asp Ala Ile Leu Lys Gln Gly Ser Lys
    1945            1950                1955 atc gtt gac ggt ctc tcg aac ttc aag cag cca gtg ttc gtc tat       8728
Ile Val Asp Gly Leu Ser Asn Phe Lys Gln Pro Val Phe Val Tyr
1960                1965                1970 gtt gtc ccc aac gga gag ctt cgt gga gga gct tgg gtc gtg ttg       8773
Val Val Pro Asn Gly Glu Leu Arg Gly Gly Ala Trp Val Val Leu
        1975            1980                1985 gat cct act atc aac ctt gcc aag atg gag atg tac gct gat gaa       8818
Asp Pro Thr Ile Asn Leu Ala Lys Met Glu Met Tyr Ala Asp Glu
            1990            1995                2000 acc gct cga gga gga att ctc gag ccg gaa ggt atc gtt gag atc       8863
Thr Ala Arg Gly Gly Ile Leu Glu Pro Glu Gly Ile Val Glu Ile
                2005            2010                2015 aag ttc cga cga gac aag gtc atc gct acc atg gag cga ttg gac       8908
Lys Phe Arg Arg Asp Lys Val Ile Ala Thr Met Glu Arg Leu Asp
                    2020            2025                2030 gag acc tat gcc tct ctc aaa gct gcc tcg aac gac tca acc aag       8953
Glu Thr Tyr Ala Ser Leu Lys Ala Ala Ser Asn Asp Ser Thr Lys
        2035            2040                2045 tct gcg gag gag cga gct aag agt gct gag cta ctc aag gca aga       8998
Ser Ala Glu Glu Arg Ala Lys Ser Ala Glu Leu Leu Lys Ala Arg
    2050            2055                2060 gag act cta ctt caa ccg acg tac ttg cag att gca cac ctt tac       9043
Glu Thr Leu Leu Gln Pro Thr Tyr Leu Gln Ile Ala His Leu Tyr
2065                2070                2075 gct gat ctc cat gat cgt gtc gga cga atg gag gcc aag ggt tgc       9088
Ala Asp Leu His Asp Arg Val Gly Arg Met Glu Ala Lys Gly Cys
        2080            2085                2090 gcg aag cga gct gtc tgg gct gag gct cga cga ttc ttc tac tgg       9133
Ala Lys Arg Ala Val Trp Ala Glu Ala Arg Arg Phe Phe Tyr Trp
            2095            2100                2105 cga ctt cga cga cgt ctc aac gat gag gtgagccgtc ccattcactc        9180
Arg Leu Arg Arg Arg Leu Asn Asp Glu
                2110            2115
```

| | | |
|---|---|---|
| tttcgttgca aggttcagta gtactaaccg cttctttctt tatctatcag cac atc<br>His Ile | | 9236 |
| ctg tct aag ttc gct gct gcc aac ccg gat ctt act ctc gag gag<br>Leu Ser Lys Phe Ala Ala Ala Asn Pro Asp Leu Thr Leu Glu Glu<br>2120                        2125                    2130 | | 9281 |
| cga caa aac att ctc gac tct gtc gtc cag act gac ctc act gat<br>Arg Gln Asn Ile Leu Asp Ser Val Val Gln Thr Asp Leu Thr Asp<br>2135                        2140                    2145 | | 9326 |
| gac cga gcc acc gct gaa tgg att gag cag tct gca gaa gag att<br>Asp Arg Ala Thr Ala Glu Trp Ile Glu Gln Ser Ala Glu Glu Ile<br>2150                        2155                    2160 | | 9371 |
| gct gct gcc gtt gcc gaa gtc cga tcc acc tac gtg tcg aat aag<br>Ala Ala Ala Val Ala Glu Val Arg Ser Thr Tyr Val Ser Asn Lys<br>2165                        2170                    2175 | | 9416 |
| att atc agc ttc gcc gag acg gag cga gct gga gcg ttg cag ggc<br>Ile Ile Ser Phe Ala Glu Thr Glu Arg Ala Gly Ala Leu Gln Gly<br>2180                        2185                    2190 | | 9461 |
| ttg gtc gct gtc ttg agc act ttg aat gcg gaa gac aag aag gcc<br>Leu Val Ala Val Leu Ser Thr Leu Asn Ala Glu Asp Lys Lys Ala<br>2195                        2200                    2205 | | 9506 |
| ctt gtt tct agc ctt ggt ctc taa attttaattt ttttgtcga tgctattctt<br>Leu Val Ser Ser Leu Gly Leu<br>2210 | | 9560 |
| cctatcttta gtctttgatt aacttttgaa tatccttcat agatctttcc ttgcatacat | | 9620 |
| tgatattatt tcctcacccg tttttatgta cttccatacg agtttccatt tttttctgct | | 9680 |
| tttatatttc gactacacgt cgactgttca cctgcctctc ttttgttctt tctgttctgt | | 9740 |
| tttcttctgt tctttcgcct cttgggattc tatattctcc ttcgcattta catatgctca | | 9800 |
| tgttaatgtc tgactcagag ttcactagga tatgtcgtga gagcccgaaa caagttgcac | | 9860 |
| aacatatatt gataatgatc agaacactct aagaccaccc agtccatgat cagccgcatc | | 9920 |
| gccagtttcg atctcttctc cattctcatc aacctcaatc tcctcccgga tcgtcctgcc | | 9980 |
| cagcagactg ccgaataact cgtcgacctg ctcctcctgc cacaagtctt ccgttcgctc | | 10040 |
| aggaaccatg aagttcatga tcttttcttg ggggtatat cgaagcttgc gaccttttaga | | 10100 |
| agctcgtgta tcgagggtgg gcttgtgctt tttgggtccg taattggaaa aggttgcttg | | 10160 |
| gcctatttca aaataaacga aattgatgat tatacaccgc cgtagaccgt ttctggtcag | | 10220 |
| gattttgtgt tggacgatga tataccgatc gatgtttgag cagacaaggg agttaggaag | | 10280 |
| agactactta ccactcatag cgccgactcc agcacctcca cctcttcgct cgatgacgtc | | 10340 |
| tctgaccaag ctctggtaaa actctttgtc atcaccccaa acggcggcct cacattcagc | | 10400 |
| ctcatcctga gagacgagtc ccatgaaccg atctactttt ttcctaccct ctagaccctc | | 10460 |
| aagggaagct ccaatttgct cgacgactcc gatcttgacg gatttaaact tttcacctcg | | 10520 |
| aagattctga aggccttgag cggtcataat cttggaagac c | | 10561 |

<210> SEQ ID NO 2
<211> LENGTH: 6645
<212> TYPE: DNA
<213> ORGANISM: Phaffia rhodozyma
<220> FEATURE:
<221> NAME/KEY: CDS
<222> LOCATION: (1)..(6645)

<400> SEQUENCE: 2

| | |
|---|---|
| atg gtt gtc gat cac gag agc gta agg cat ttc atc ggt gga aac gca<br>Met Val Val Asp His Glu Ser Val Arg His Phe Ile Gly Gly Asn Ala<br>1              5                    10                    15 | 48 |

```
ctt gag aac gcc cct ccg tca agc gtc acc gat ttc gtt aga agt caa      96
Leu Glu Asn Ala Pro Pro Ser Ser Val Thr Asp Phe Val Arg Ser Gln
         20                  25                  30 gat ggt cac acg gtc atc acc aaa gtc ctc att gcc aac aac gga atc     144
Asp Gly His Thr Val Ile Thr Lys Val Leu Ile Ala Asn Asn Gly Ile
             35                  40                  45 gct gct gta aaa gag atc cga tca gtt cgt aaa tgg gct tac gag acg     192
Ala Ala Val Lys Glu Ile Arg Ser Val Arg Lys Trp Ala Tyr Glu Thr
     50                  55                  60 ttt gga gat gag cga gcc atc gaa ttt acg gta atg gcc act cca gaa     240
Phe Gly Asp Glu Arg Ala Ile Glu Phe Thr Val Met Ala Thr Pro Glu
 65                  70                  75                  80 gat ttg aag gtg aac tgc gac tat att cga atg gct gat cga gtc gtc     288
Asp Leu Lys Val Asn Cys Asp Tyr Ile Arg Met Ala Asp Arg Val Val
                 85                  90                  95 gaa gtt cct gga gga act aac aac aac aat cac tct aac gtc gac ctc     336
Glu Val Pro Gly Gly Thr Asn Asn Asn Asn His Ser Asn Val Asp Leu
            100                 105                 110 atc gtt gac att gcc gag cga ttc aat ata cat gct gtt tgg gct gga     384
Ile Val Asp Ile Ala Glu Arg Phe Asn Ile His Ala Val Trp Ala Gly
        115                 120                 125 tgg ggt cac gct tcg gaa aac ccc aga ctt ccc gag tct ctc gcc gcc     432
Trp Gly His Ala Ser Glu Asn Pro Arg Leu Pro Glu Ser Leu Ala Ala
    130                 135                 140 tca aag aac aag atc gtc ttc att ggt cct ccc gga tcc gct atg cga     480
Ser Lys Asn Lys Ile Val Phe Ile Gly Pro Pro Gly Ser Ala Met Arg
145                 150                 155                 160 tcc ctt gga gac aag att tct tcg acc atc gtt gcc cag tct gcc cag     528
Ser Leu Gly Asp Lys Ile Ser Ser Thr Ile Val Ala Gln Ser Ala Gln
                165                 170                 175 gtg ccg tgt atg gcc tgg tct gga tca ggc atc act gat aca gag ctc     576
Val Pro Cys Met Ala Trp Ser Gly Ser Gly Ile Thr Asp Thr Glu Leu
            180                 185                 190 agc cct cag ggc ttc gtg act gtg ccc gat ggg cca tat cag gct gct     624
Ser Pro Gln Gly Phe Val Thr Val Pro Asp Gly Pro Tyr Gln Ala Ala
        195                 200                 205 tgt gta aag acg gtg gag gat ggt ttg gtg cga gcc gag aag atc ggt     672
Cys Val Lys Thr Val Glu Asp Gly Leu Val Arg Ala Glu Lys Ile Gly
    210                 215                 220 ttg cca gtt atg atc aag gcc tct gag gga gga gga gga aag ggt atc     720
Leu Pro Val Met Ile Lys Ala Ser Glu Gly Gly Gly Gly Lys Gly Ile
225                 230                 235                 240 cga atg gtt cac agc atg gac aca ttc aag aac tcc tac aac tcc gtc     768
Arg Met Val His Ser Met Asp Thr Phe Lys Asn Ser Tyr Asn Ser Val
                245                 250                 255 gct tcc gag gtg cca gga tct ccg att ttc atc atg gcc ttg gct gga     816
Ala Ser Glu Val Pro Gly Ser Pro Ile Phe Ile Met Ala Leu Ala Gly
            260                 265                 270 tct gct cga cat ttg gag gtc cag ctc ctt gct gat cag tac gga aac     864
Ser Ala Arg His Leu Glu Val Gln Leu Leu Ala Asp Gln Tyr Gly Asn
        275                 280                 285 gct atc tct ttg ttc ggt cga gat tgc tct gtt cag cga cga cat cag     912
Ala Ile Ser Leu Phe Gly Arg Asp Cys Ser Val Gln Arg Arg His Gln
    290                 295                 300 aag atc att gag gag gct ccc gtc acg atc gct cgt cca gag aga ttc     960
Lys Ile Ile Glu Glu Ala Pro Val Thr Ile Ala Arg Pro Glu Arg Phe
305                 310                 315                 320 gaa gag atg gag aag gct gct gtc agg ttg gcc aag tta gta gga tat    1008
Glu Glu Met Glu Lys Ala Ala Val Arg Leu Ala Lys Leu Val Gly Tyr
```

```
                325              330              335
gtt agt gcc ggt acc gtc gaa tac ctc tac tct cac gcc gac gac tca    1056
Val Ser Ala Gly Thr Val Glu Tyr Leu Tyr Ser His Ala Asp Asp Ser
            340              345              350 ttc ttc ttc ctc gaa ctc aac cct cga ctt caa gtc gag cac cct act    1104
Phe Phe Phe Leu Glu Leu Asn Pro Arg Leu Gln Val Glu His Pro Thr
        355              360              365 acc gag atg gtc tcg ggt gtc aac ctt ccc gct gct cag ctt cag att    1152
Thr Glu Met Val Ser Gly Val Asn Leu Pro Ala Ala Gln Leu Gln Ile
    370              375              380 gct atg ggt atc cct ctt tct cga att cgg gat att cga gtc ctc tac    1200
Ala Met Gly Ile Pro Leu Ser Arg Ile Arg Asp Ile Arg Val Leu Tyr
385              390              395              400 ggt ctc gat ccc cac act gtt tcc gag atc gac ttc gac agc agc aga    1248
Gly Leu Asp Pro His Thr Val Ser Glu Ile Asp Phe Asp Ser Ser Arg
            405              410              415 gcg gag tct gtc cag act cag agg aag cct agg ccc aag ggt cac gtc    1296
Ala Glu Ser Val Gln Thr Gln Arg Lys Pro Arg Pro Lys Gly His Val
        420              425              430 att gcc tgt cga atc acg agt gaa aac ccc gat gag ggg ttc aag ccg    1344
Ile Ala Cys Arg Ile Thr Ser Glu Asn Pro Asp Glu Gly Phe Lys Pro
    435              440              445 tct gcc gga gat atc caa gag ttg aac ttc aga agt aat act aac gtc    1392
Ser Ala Gly Asp Ile Gln Glu Leu Asn Phe Arg Ser Asn Thr Asn Val
450              455              460 tgg gga tac ttc tct gtt gga gct act gga gga att cat agt ttc gcc    1440
Trp Gly Tyr Phe Ser Val Gly Ala Thr Gly Gly Ile His Ser Phe Ala
465              470              475              480 gat tct caa ttc ggt cac gtg ttt gct tat ggc tcc gac cga acg act    1488
Asp Ser Gln Phe Gly His Val Phe Ala Tyr Gly Ser Asp Arg Thr Thr
            485              490              495 gcc aga aag aat atg gtt atc gcc ttg aaa gag ctt tcc att cga gga    1536
Ala Arg Lys Asn Met Val Ile Ala Leu Lys Glu Leu Ser Ile Arg Gly
        500              505              510 gac ttc cga acc act gtc gag tat ctt atc act ctt ctt gag acg agc    1584
Asp Phe Arg Thr Thr Val Glu Tyr Leu Ile Thr Leu Leu Glu Thr Ser
    515              520              525 gat ttc gag cag aac gcc att acc acc gct tgg ttg gat ggg ttg atc    1632
Asp Phe Glu Gln Asn Ala Ile Thr Thr Ala Trp Leu Asp Gly Leu Ile
530              535              540 act aac aag ctt aca tct gag agg cct gat cca tca ctg gcc gtt att    1680
Thr Asn Lys Leu Thr Ser Glu Arg Pro Asp Pro Ser Leu Ala Val Ile
545              550              555              560 tgt ggt gca att gtg aaa gct cac gtg gct tct gag aac tgt tgg gcc    1728
Cys Gly Ala Ile Val Lys Ala His Val Ala Ser Glu Asn Cys Trp Ala
            565              570              575 gaa tac cga cga gta ttg gac aag gga cag gtt ccc tcc aag gac act    1776
Glu Tyr Arg Arg Val Leu Asp Lys Gly Gln Val Pro Ser Lys Asp Thr
        580              585              590 ctc aag aca gtg ttc act ctt gat ttc atc tat gag ggt gtt cgg tac    1824
Leu Lys Thr Val Phe Thr Leu Asp Phe Ile Tyr Glu Gly Val Arg Tyr
    595              600              605 aat ttc acc gct gct cga gcc tcc ctc aac act tac cga ttg tat cta    1872
Asn Phe Thr Ala Ala Arg Ala Ser Leu Asn Thr Tyr Arg Leu Tyr Leu
610              615              620 aac gga gga aag acc gtg gtg tcc atc cga cct ttg gcc gat ggt gga    1920
Asn Gly Gly Lys Thr Val Val Ser Ile Arg Pro Leu Ala Asp Gly Gly
625              630              635              640 atg ctc gtt ctt ctc gat ggc cga tcc cac act ctc tac tgg agg gag    1968
```

```
Met Leu Val Leu Leu Asp Gly Arg Ser His Thr Leu Tyr Trp Arg Glu
            645                 650                 655 gaa gtc ggt acc ctc cga att cag gta gac gca aag act tgc ctg att        2016
Glu Val Gly Thr Leu Arg Ile Gln Val Asp Ala Lys Thr Cys Leu Ile
            660                 665                 670 gag cag gag aac gac ccc act cag ctc cga tca ccc tcg cct gga aag        2064
Glu Gln Glu Asn Asp Pro Thr Gln Leu Arg Ser Pro Ser Pro Gly Lys
            675                 680                 685 atc atc cgg ttt ttg gtc gaa agc gga gat cac atc tcc tcc gga gat        2112
Ile Ile Arg Phe Leu Val Glu Ser Gly Asp His Ile Ser Ser Gly Asp
            690                 695                 700 atc tat gct gag gtt gag gtc atg aag atg atc ttg ccc ttg att gcc        2160
Ile Tyr Ala Glu Val Glu Val Met Lys Met Ile Leu Pro Leu Ile Ala
705                 710                 715                 720 cag gag tcc ggt cac gtt cag ttt gtc aag caa gcc ggt gtg acc gtc        2208
Gln Glu Ser Gly His Val Gln Phe Val Lys Gln Ala Gly Val Thr Val
                    725                 730                 735 gat cct gga gcg att att ggg atc ttg agt ctt gat gac cct acg cga        2256
Asp Pro Gly Ala Ile Ile Gly Ile Leu Ser Leu Asp Asp Pro Thr Arg
                740                 745                 750 gtg aag aag gcg aag ccc ttc gag ggt ctc ctg cct gtg act ggt ctc        2304
Val Lys Lys Ala Lys Pro Phe Glu Gly Leu Leu Pro Val Thr Gly Leu
            755                 760                 765 cct aac ctg ccc ggt aac aga cct cac cag cgg cta cag ttc cag ctt        2352
Pro Asn Leu Pro Gly Asn Arg Pro His Gln Arg Leu Gln Phe Gln Leu
        770                 775                 780 gag tcg ata tac tcg gtc ttg gat gga tac gag agt gac tcc act gca        2400
Glu Ser Ile Tyr Ser Val Leu Asp Gly Tyr Glu Ser Asp Ser Thr Ala
785                 790                 795                 800 aca atc ctc cga tca ttc tct gaa aac ctt tat gat cct gat ctt gct        2448
Thr Ile Leu Arg Ser Phe Ser Glu Asn Leu Tyr Asp Pro Asp Leu Ala
                805                 810                 815 ttc gga gag gct tta tcc atc att tcc gtc ctt tct ggg aga atg cct        2496
Phe Gly Glu Ala Leu Ser Ile Ile Ser Val Leu Ser Gly Arg Met Pro
                820                 825                 830 gcc gat ctt gag gag agc att cga gag gtc atc agc gaa gct cag tcg        2544
Ala Asp Leu Glu Glu Ser Ile Arg Glu Val Ile Ser Glu Ala Gln Ser
            835                 840                 845 aag cct cac gcc gag ttc cct gga tca aag atc ctc aaa gtc gtc gag        2592
Lys Pro His Ala Glu Phe Pro Gly Ser Lys Ile Leu Lys Val Val Glu
        850                 855                 860 cgg tac atc gat aat ttg cga cct cag gag agg gct atg gtc cga act        2640
Arg Tyr Ile Asp Asn Leu Arg Pro Gln Glu Arg Ala Met Val Arg Thr
865                 870                 875                 880 cag atc gaa ccc atc gtt ggt att gct gag aag aac gtt ggc ggt cct        2688
Gln Ile Glu Pro Ile Val Gly Ile Ala Glu Lys Asn Val Gly Gly Pro
                885                 890                 895 aag ggt tac gcc tct tac gtc tta gct acc atc ctt caa aag ttc ttg        2736
Lys Gly Tyr Ala Ser Tyr Val Leu Ala Thr Ile Leu Gln Lys Phe Leu
                900                 905                 910 gcc gtt gag gcc gtt ttt gct act ggt agt gaa gag gcc att gtt ctc        2784
Ala Val Glu Ala Val Phe Ala Thr Gly Ser Glu Glu Ala Ile Val Leu
            915                 920                 925 caa ctt cga gat gaa aac cga gaa tct ttg aac gac gtc ctt ggt ctc        2832
Gln Leu Arg Asp Glu Asn Arg Glu Ser Leu Asn Asp Val Leu Gly Leu
        930                 935                 940 gtc ctg gct cac tcg cgt ctc agc gct cga tcc aag ctt gtt ctc tcc        2880
Val Leu Ala His Ser Arg Leu Ser Ala Arg Ser Lys Leu Val Leu Ser
945                 950                 955                 960
```

-continued

```
gtc ttt gat ctg atc aag tct atg cag ctc ctc aac aac act gag ggt        2928
Val Phe Asp Leu Ile Lys Ser Met Gln Leu Leu Asn Asn Thr Glu Gly
            965                 970                 975 tct ttc ctt cat aag act atg aaa gcg ctt gcc gac atg ccc acc aag        2976
Ser Phe Leu His Lys Thr Met Lys Ala Leu Ala Asp Met Pro Thr Lys
        980                 985                 990 gct cct ttg gcc agc aag gtg tct ttg aag gct cgg gaa att ctt atc        3024
Ala Pro Leu Ala Ser Lys Val Ser Leu Lys Ala Arg Glu Ile Leu Ile
        995                 1000                1005 tct tgc tct ctt ccc tct tac gag gag agg ttg ttc cag atg gaa            3069
Ser Cys Ser Leu Pro Ser Tyr Glu Glu Arg Leu Phe Gln Met Glu
    1010                1015                1020 aag atc ctt aac tct tct gtc acc act tct tac tac gga gag act            3114
Lys Ile Leu Asn Ser Ser Val Thr Thr Ser Tyr Tyr Gly Glu Thr
    1025                1030                1035 gga ggt gga cac aga aac cct tcg gtt gat gtt ctg act gag atc            3159
Gly Gly Gly His Arg Asn Pro Ser Val Asp Val Leu Thr Glu Ile
    1040                1045                1050 tca aac tct cga ttc acc gtc tac gat gtc ctg tcc tcc ttc ttc            3204
Ser Asn Ser Arg Phe Thr Val Tyr Asp Val Leu Ser Ser Phe Phe
    1055                1060                1065 aag cac gat gat cct tgg att gtt ctt gct agt ttg acc gtc tac            3249
Lys His Asp Asp Pro Trp Ile Val Leu Ala Ser Leu Thr Val Tyr
    1070                1075                1080 gtt ctt cga gct tac cga gag tac agt att ctt gat atg caa cat            3294
Val Leu Arg Ala Tyr Arg Glu Tyr Ser Ile Leu Asp Met Gln His
    1085                1090                1095 gag caa ggt cag gat ggc gct gct gga gtc atc act tgg cga ttc            3339
Glu Gln Gly Gln Asp Gly Ala Ala Gly Val Ile Thr Trp Arg Phe
    1100                1105                1110 aag ctc aac cag ccc atc gct gag tct tct act ccc cga gtt gac            3384
Lys Leu Asn Gln Pro Ile Ala Glu Ser Ser Thr Pro Arg Val Asp
    1115                1120                1125 tcg aat cga gac gtt tac cga gtc ggt tcg ctt tct gat ttg acc            3429
Ser Asn Arg Asp Val Tyr Arg Val Gly Ser Leu Ser Asp Leu Thr
    1130                1135                1140 tac aag atc aag cag agt cag acc gag ccc ctc cga gct ggt gtc            3474
Tyr Lys Ile Lys Gln Ser Gln Thr Glu Pro Leu Arg Ala Gly Val
    1145                1150                1155 atg acg agc ttc aac aac ttg aag gag gtt cag gac gga ctc ttg            3519
Met Thr Ser Phe Asn Asn Leu Lys Glu Val Gln Asp Gly Leu Leu
    1160                1165                1170 aat gtt ctg tct ttc ttc cct gct tac cat cat caa gat ttc act            3564
Asn Val Leu Ser Phe Phe Pro Ala Tyr His His Gln Asp Phe Thr
    1175                1180                1185 caa cga cat ggt cag gac agt gcc atg ccc aac gtt ctc aac att            3609
Gln Arg His Gly Gln Asp Ser Ala Met Pro Asn Val Leu Asn Ile
    1190                1195                1200 gct atc cgg gct ttc gag gag aag gac gac atg tct gat ctt gat            3654
Ala Ile Arg Ala Phe Glu Glu Lys Asp Asp Met Ser Asp Leu Asp
    1205                1210                1215 tgg gcc aag agt gtt gag tcg ctg gta atg cag atg tct gcc gag            3699
Trp Ala Lys Ser Val Glu Ser Leu Val Met Gln Met Ser Ala Glu
    1220                1225                1230 atc cag aag aag gga att cga cga gtt acc ttg gtt tgc cga                3744
Ile Gln Lys Lys Gly Ile Arg Arg Val Thr Phe Leu Val Cys Arg
    1235                1240                1245 aag ggc gtt tac ccc tcc tac ttc acc ttc aga caa gag ggt gcc            3789
Lys Gly Val Tyr Pro Ser Tyr Phe Thr Phe Arg Gln Glu Gly Ala
    1250                1255                1260
```

-continued

| | |
|---|---|
| cag ggc ccc tgg aga gag gag gag aag att cga aac atc gag cct<br>Gln Gly Pro Trp Arg Glu Glu Glu Lys Ile Arg Asn Ile Glu Pro<br>1265                              1270                            1275 | 3834 |
| gct cta gcc agt cag ctt gag ctc aac cga ctc tcg aat ttc aag<br>Ala Leu Ala Ser Gln Leu Glu Leu Asn Arg Leu Ser Asn Phe Lys<br>1280                              1285                            1290 | 3879 |
| gtc acc cct atc ttc gta gac aac aga cag atc cac atc tac aag<br>Val Thr Pro Ile Phe Val Asp Asn Arg Gln Ile His Ile Tyr Lys<br>1295                              1300                            1305 | 3924 |
| gga gtg ggt aag gag aac tct tcc gat gtt cga ttc ttt atc cgg<br>Gly Val Gly Lys Glu Asn Ser Ser Asp Val Arg Phe Phe Ile Arg<br>1310                              1315                            1320 | 3969 |
| gct ttg gtt cga cct gga cgg gtc cag gga tcg atg aag gct gcc<br>Ala Leu Val Arg Pro Gly Arg Val Gln Gly Ser Met Lys Ala Ala<br>1325                              1330                            1335 | 4014 |
| gag tat ctc atc tcc gag tgc gat cga ctg ctc act gat atc ctg<br>Glu Tyr Leu Ile Ser Glu Cys Asp Arg Leu Leu Thr Asp Ile Leu<br>1340                              1345                            1350 | 4059 |
| gac gcc ttg gag gtt gtt gga gcc gag act cga aac gcc gat tgc<br>Asp Ala Leu Glu Val Val Gly Ala Glu Thr Arg Asn Ala Asp Cys<br>1355                              1360                            1365 | 4104 |
| aac cat gtt gga att aac ttc atc tat aac gtt ctt gtc gac ttc<br>Asn His Val Gly Ile Asn Phe Ile Tyr Asn Val Leu Val Asp Phe<br>1370                              1375                            1380 | 4149 |
| gac gac gtc cag gag gcc ctt gcc ggg ttc att gag agg cac gga<br>Asp Asp Val Gln Glu Ala Leu Ala Gly Phe Ile Glu Arg His Gly<br>1385                              1390                            1395 | 4194 |
| aag agg ctt tgg cga ctt cga gtg acc gct tct gaa atc cga atg<br>Lys Arg Leu Trp Arg Leu Arg Val Thr Ala Ser Glu Ile Arg Met<br>1400                              1405                            1410 | 4239 |
| gtt ctt gag gac gac gag ggt aac gtc acc ccc atc cga tgc tgc<br>Val Leu Glu Asp Asp Glu Gly Asn Val Thr Pro Ile Arg Cys Cys<br>1415                              1420                            1425 | 4284 |
| att gag aac gtt tct ggt ttc gtc gtg aag tac cac gcc tac cag<br>Ile Glu Asn Val Ser Gly Phe Val Val Lys Tyr His Ala Tyr Gln<br>1430                              1435                            1440 | 4329 |
| gag gtt gag acc gag aag ggt act acc atc ttg aag tca atc gga<br>Glu Val Glu Thr Glu Lys Gly Thr Thr Ile Leu Lys Ser Ile Gly<br>1445                              1450                            1455 | 4374 |
| gac ctt gga cct ctt cac ctt cag cct gtc aac cat gct tac cag<br>Asp Leu Gly Pro Leu His Leu Gln Pro Val Asn His Ala Tyr Gln<br>1460                              1465                            1470 | 4419 |
| acc aag aac agt ctt cag ccc cga cga tac cag gct cac ttg gtt<br>Thr Lys Asn Ser Leu Gln Pro Arg Arg Tyr Gln Ala His Leu Val<br>1475                              1480                            1485 | 4464 |
| gga acg act tac gtc tac gac tac ccc gat ctc ttc gtt cag agt<br>Gly Thr Thr Tyr Val Tyr Asp Tyr Pro Asp Leu Phe Val Gln Ser<br>1490                              1495                            1500 | 4509 |
| ttg cgc aag gtt tgg gct gag gct gct gct aag att cct cac ctc<br>Leu Arg Lys Val Trp Ala Glu Ala Ala Ala Lys Ile Pro His Leu<br>1505                              1510                            1515 | 4554 |
| cgg gtg cct agc gag cct ctt acc gct acc gag ttg gtt ctc gat<br>Arg Val Pro Ser Glu Pro Leu Thr Ala Thr Glu Leu Val Leu Asp<br>1520                              1525                            1530 | 4599 |
| gag aac aac gag ctt cag gag gtc gag cga cct ccg ggt tcc aac<br>Glu Asn Asn Glu Leu Gln Glu Val Glu Arg Pro Pro Gly Ser Asn<br>1535                              1540                            1545 | 4644 |
| tcg tgt ggt atg gtc gcc tgg atc ttc act atg ctc act ccc gag<br>Ser Cys Gly Met Val Ala Trp Ile Phe Thr Met Leu Thr Pro Glu | 4689 |

-continued

```
                   1550                1555                1560
tat ccc aag ggt cga cga gta gtt gcc att gcc aac gat atc acc        4734
Tyr Pro Lys Gly Arg Arg Val Val Ala Ile Ala Asn Asp Ile Thr
    1565                1570                1575 ttc aag att gga tcc ttt ggt cct aag gaa gac gat tac ttc ttc        4779
Phe Lys Ile Gly Ser Phe Gly Pro Lys Glu Asp Asp Tyr Phe Phe
    1580                1585                1590 aag gct act gaa att gcc aag aag ctg ggc ctt cct cga att tac        4824
Lys Ala Thr Glu Ile Ala Lys Lys Leu Gly Leu Pro Arg Ile Tyr
    1595                1600                1605 ctc tct gcc aac agt gga gct aga ctc ggt atc gcg gag gag ctc        4869
Leu Ser Ala Asn Ser Gly Ala Arg Leu Gly Ile Ala Glu Glu Leu
    1610                1615                1620 ttg cac atc ttc aag gcg gcc ttc gtt gac ccc gca aag cct tcc        4914
Leu His Ile Phe Lys Ala Ala Phe Val Asp Pro Ala Lys Pro Ser
    1625                1630                1635 atg ggt att aag tat cta tac ttg acc cct gaa act tta tcc act        4959
Met Gly Ile Lys Tyr Leu Tyr Leu Thr Pro Glu Thr Leu Ser Thr
    1640                1645                1650 ctt gcc aag aag gga tcc agc gtc acc act gag gag atc gag gat        5004
Leu Ala Lys Lys Gly Ser Ser Val Thr Thr Glu Glu Ile Glu Asp
    1655                1660                1665 gac ggc gag cga cga cac aag atc acc gcc atc atc ggt ctt gca        5049
Asp Gly Glu Arg Arg His Lys Ile Thr Ala Ile Ile Gly Leu Ala
    1670                1675                1680 gag ggt ttg gga gtt gag tct ctt cga gga tcc ggt ctt att gct        5094
Glu Gly Leu Gly Val Glu Ser Leu Arg Gly Ser Gly Leu Ile Ala
    1685                1690                1695 gga gcc acc act cga gct tac gag gag gga atc ttc acc atc tct        5139
Gly Ala Thr Thr Arg Ala Tyr Glu Glu Gly Ile Phe Thr Ile Ser
    1700                1705                1710 ctc gtt act gcc cga tcg gtc ggt atc gga gct tac ttg gtt cga        5184
Leu Val Thr Ala Arg Ser Val Gly Ile Gly Ala Tyr Leu Val Arg
    1715                1720                1725 ttg ggt cag cga gct att cag gtt gaa ggc aac cct atg atc ctt        5229
Leu Gly Gln Arg Ala Ile Gln Val Glu Gly Asn Pro Met Ile Leu
    1730                1735                1740 act gga gct cag tct ctc aac aag gtg ctt gga cga gag gtt tac        5274
Thr Gly Ala Gln Ser Leu Asn Lys Val Leu Gly Arg Glu Val Tyr
    1745                1750                1755 act tcc aac ctt cag ctt gga gga acc cag att atg gcc cga aac        5319
Thr Ser Asn Leu Gln Leu Gly Gly Thr Gln Ile Met Ala Arg Asn
    1760                1765                1770 ggt acc acg cat ctc gtc gct gaa tct gat ctc gat ggt gct ctc        5364
Gly Thr Thr His Leu Val Ala Glu Ser Asp Leu Asp Gly Ala Leu
    1775                1780                1785 aag gtc atc cag tgg ctc tcg tat gtg ccc gag cga aag ggc aag        5409
Lys Val Ile Gln Trp Leu Ser Tyr Val Pro Glu Arg Lys Gly Lys
    1790                1795                1800 gcc att cct atc tgg cct tcc gag gac cct tgg gac cga act gtg        5454
Ala Ile Pro Ile Trp Pro Ser Glu Asp Pro Trp Asp Arg Thr Val
    1805                1810                1815 acc tac gag cct ccc cga ggt cct tac gat cct cga tgg ttg ctt        5499
Thr Tyr Glu Pro Pro Arg Gly Pro Tyr Asp Pro Arg Trp Leu Leu
    1820                1825                1830 gaa gga aag ccg gat gaa ggc ttg act ggt ctt ttc gac aag gga        5544
Glu Gly Lys Pro Asp Glu Gly Leu Thr Gly Leu Phe Asp Lys Gly
    1835                1840                1845 tct ttc atg gag acc ctt gga gat tgg gcc aag act atc gtc acc        5589
```

-continued

```
            Ser Phe Met Glu Thr Leu Gly Asp Trp Ala Lys Thr Ile Val Thr
                1850                1855                1860 ggt cga gcc cga ctg gga ggc att cct atg ggt gtt att gct gtc       5634
Gly Arg Ala Arg Leu Gly Gly Ile Pro Met Gly Val Ile Ala Val
    1865                1870                1875 gaa acc agg acg acc gag aag atc atc gct gcc gat cct gcc aac       5679
Glu Thr Arg Thr Thr Glu Lys Ile Ile Ala Ala Asp Pro Ala Asn
    1880                1885                1890 cct gca gct ttc gag caa aag att atg gag gct ggt cag gtt tgg       5724
Pro Ala Ala Phe Glu Gln Lys Ile Met Glu Ala Gly Gln Val Trp
    1895                1900                1905 aac ccc aac gct gct tac aag acc gct caa tcc atc ttt gat atc       5769
Asn Pro Asn Ala Ala Tyr Lys Thr Ala Gln Ser Ile Phe Asp Ile
    1910                1915                1920 aac aag gag ggt ctt cct ttg atg atc ctt gcc aac atc cga ggt       5814
Asn Lys Glu Gly Leu Pro Leu Met Ile Leu Ala Asn Ile Arg Gly
    1925                1930                1935 ttc tct gga gga cag ggt gat atg ttt gac gct atc ctc aag cag       5859
Phe Ser Gly Gly Gln Gly Asp Met Phe Asp Ala Ile Leu Lys Gln
    1940                1945                1950 ggt tct aag atc gtt gac ggt ctc tcg aac ttc aag cag cca gtg       5904
Gly Ser Lys Ile Val Asp Gly Leu Ser Asn Phe Lys Gln Pro Val
    1955                1960                1965 ttc gtc tat gtt gtc ccc aac gga gag ctt cgt gga gga gct tgg       5949
Phe Val Tyr Val Val Pro Asn Gly Glu Leu Arg Gly Gly Ala Trp
    1970                1975                1980 gtg gtg ttg gat cct act atc aac ctt gcc aag atg gag atg tac       5994
Val Val Leu Asp Pro Thr Ile Asn Leu Ala Lys Met Glu Met Tyr
    1985                1990                1995 gct gat gaa acc gct cga gga gga att ctc gag ccg gaa ggt atc       6039
Ala Asp Glu Thr Ala Arg Gly Gly Ile Leu Glu Pro Glu Gly Ile
    2000                2005                2010 gtt gag atc aag ttc cga cga gac aag gtc atc gct acc atg gag       6084
Val Glu Ile Lys Phe Arg Arg Asp Lys Val Ile Ala Thr Met Glu
    2015                2020                2025 cga ttg gac gag acc tat gcc tct ctc aaa gct gcc tcg aac gac       6129
Arg Leu Asp Glu Thr Tyr Ala Ser Leu Lys Ala Ala Ser Asn Asp
    2030                2035                2040 tca acc aag tct gcg gag gag cga gct aag agt gct gag cta ctc       6174
Ser Thr Lys Ser Ala Glu Glu Arg Ala Lys Ser Ala Glu Leu Leu
    2045                2050                2055 aag gca aga gag act cta ctt caa ccg acg tac ttg cag att gca       6219
Lys Ala Arg Glu Thr Leu Leu Gln Pro Thr Tyr Leu Gln Ile Ala
    2060                2065                2070 cac ctt tac gct gat ctc cat gat cgt gtc gga cga atg gag gcc       6264
His Leu Tyr Ala Asp Leu His Asp Arg Val Gly Arg Met Glu Ala
    2075                2080                2085 aag ggt tgc gcg aag cga gct gtc tgg gct gag gct cga cga ttc       6309
Lys Gly Cys Ala Lys Arg Ala Val Trp Ala Glu Ala Arg Arg Phe
    2090                2095                2100 ttc tac tgg cga ctt cga cga cgt ctc aac gat gag cac atc ctg       6354
Phe Tyr Trp Arg Leu Arg Arg Arg Leu Asn Asp Glu His Ile Leu
    2105                2110                2115 tct aag ttc gct gct gcc aac ccg gat ctt act ctc gag gag cga       6399
Ser Lys Phe Ala Ala Ala Asn Pro Asp Leu Thr Leu Glu Glu Arg
    2120                2125                2130 caa aac att ctc gac tct gtc gtc cag act gac ctc act gat gac       6444
Gln Asn Ile Leu Asp Ser Val Val Gln Thr Asp Leu Thr Asp Asp
    2135                2140                2145
```

-continued

```
cga gcc acc gct gaa tgg att gag cag tct gca gaa gag att gct      6489
Arg Ala Thr Ala Glu Trp Ile Glu Gln Ser Ala Glu Glu Ile Ala
    2150                2155                2160 gct gcc gtt gcc gaa gtc cga tcc acc tac gtg tcg aat aag att      6534
Ala Ala Val Ala Glu Val Arg Ser Thr Tyr Val Ser Asn Lys Ile
2165                2170                2175 atc agc ttc gcc gag acg gag cga gct gga gcg ttg cag ggc ttg      6579
Ile Ser Phe Ala Glu Thr Glu Arg Ala Gly Ala Leu Gln Gly Leu
    2180                2185                2190 gtc gct gtc ttg agc act ttg aat gcg gaa gac aag aag gcc ctt      6624
Val Ala Val Leu Ser Thr Leu Asn Ala Glu Asp Lys Lys Ala Leu
2195                2200                2205 gtt tct agc ctt ggt ctc taa                                      6645
Val Ser Ser Leu Gly Leu
    2210
```

<210> SEQ ID NO 3
<211> LENGTH: 2214
<212> TYPE: PRT
<213> ORGANISM: Phaffia rhodozyma

<400> SEQUENCE: 3

```
Met Val Val Asp His Glu Ser Val Arg His Phe Ile Gly Gly Asn Ala
1               5                   10                  15

Leu Glu Asn Ala Pro Pro Ser Ser Val Thr Asp Phe Val Arg Ser Gln
            20                  25                  30

Asp Gly His Thr Val Ile Thr Lys Val Leu Ile Ala Asn Asn Gly Ile
        35                  40                  45

Ala Ala Val Lys Glu Ile Arg Ser Val Arg Lys Trp Ala Tyr Glu Thr
    50                  55                  60

Phe Gly Asp Glu Arg Ala Ile Glu Phe Thr Val Met Ala Thr Pro Glu
65                  70                  75                  80

Asp Leu Lys Val Asn Cys Asp Tyr Ile Arg Met Ala Asp Arg Val Val
                85                  90                  95

Glu Val Pro Gly Gly Thr Asn Asn Asn His Ser Asn Val Asp Leu
            100                 105                 110

Ile Val Asp Ile Ala Glu Arg Phe Asn Ile His Ala Val Trp Ala Gly
        115                 120                 125

Trp Gly His Ala Ser Glu Asn Pro Arg Leu Pro Glu Ser Leu Ala Ala
    130                 135                 140

Ser Lys Asn Lys Ile Val Phe Ile Gly Pro Pro Gly Ser Ala Met Arg
145                 150                 155                 160

Ser Leu Gly Asp Lys Ile Ser Ser Thr Ile Val Ala Gln Ser Ala Gln
                165                 170                 175

Val Pro Cys Met Ala Trp Ser Gly Ser Gly Ile Thr Asp Thr Glu Leu
            180                 185                 190

Ser Pro Gln Gly Phe Val Thr Val Pro Asp Gly Pro Tyr Gln Ala Ala
        195                 200                 205

Cys Val Lys Thr Val Glu Asp Gly Leu Val Arg Ala Glu Lys Ile Gly
    210                 215                 220

Leu Pro Val Met Ile Lys Ala Ser Glu Gly Gly Gly Lys Gly Ile
225                 230                 235                 240

Arg Met Val His Ser Met Asp Thr Phe Lys Asn Ser Tyr Asn Ser Val
                245                 250                 255

Ala Ser Glu Val Pro Gly Ser Pro Ile Phe Ile Met Ala Leu Ala Gly
            260                 265                 270
```

```
Ser Ala Arg His Leu Glu Val Gln Leu Leu Ala Asp Gln Tyr Gly Asn
        275                 280                 285
Ala Ile Ser Leu Phe Gly Arg Asp Cys Ser Val Gln Arg Arg His Gln
    290                 295                 300
Lys Ile Ile Glu Glu Ala Pro Val Thr Ile Ala Arg Pro Glu Arg Phe
305                 310                 315                 320
Glu Glu Met Glu Lys Ala Ala Val Arg Leu Ala Lys Leu Val Gly Tyr
                325                 330                 335
Val Ser Ala Gly Thr Val Glu Tyr Leu Tyr Ser His Ala Asp Asp Ser
            340                 345                 350
Phe Phe Phe Leu Glu Leu Asn Pro Arg Leu Gln Val Glu His Pro Thr
        355                 360                 365
Thr Glu Met Val Ser Gly Val Asn Leu Pro Ala Ala Gln Leu Gln Ile
    370                 375                 380
Ala Met Gly Ile Pro Leu Ser Arg Ile Arg Asp Ile Arg Val Leu Tyr
385                 390                 395                 400
Gly Leu Asp Pro His Thr Val Ser Glu Ile Asp Phe Asp Ser Ser Arg
                405                 410                 415
Ala Glu Ser Val Gln Thr Gln Arg Lys Pro Arg Pro Lys Gly His Val
            420                 425                 430
Ile Ala Cys Arg Ile Thr Ser Glu Asn Pro Asp Glu Gly Phe Lys Pro
        435                 440                 445
Ser Ala Gly Asp Ile Gln Glu Leu Asn Phe Arg Ser Asn Thr Asn Val
    450                 455                 460
Trp Gly Tyr Phe Ser Val Gly Ala Thr Gly Gly Ile His Ser Phe Ala
465                 470                 475                 480
Asp Ser Gln Phe Gly His Val Phe Ala Tyr Gly Ser Asp Arg Thr Thr
                485                 490                 495
Ala Arg Lys Asn Met Val Ile Ala Leu Lys Glu Leu Ser Ile Arg Gly
            500                 505                 510
Asp Phe Arg Thr Thr Val Glu Tyr Leu Ile Thr Leu Leu Glu Thr Ser
        515                 520                 525
Asp Phe Glu Gln Asn Ala Ile Thr Thr Ala Trp Leu Asp Gly Leu Ile
    530                 535                 540
Thr Asn Lys Leu Thr Ser Glu Arg Pro Asp Pro Ser Leu Ala Val Ile
545                 550                 555                 560
Cys Gly Ala Ile Val Lys Ala His Val Ala Ser Glu Asn Cys Trp Ala
                565                 570                 575
Glu Tyr Arg Arg Val Leu Asp Lys Gly Gln Val Pro Ser Lys Asp Thr
            580                 585                 590
Leu Lys Thr Val Phe Thr Leu Asp Phe Ile Tyr Glu Gly Val Arg Tyr
        595                 600                 605
Asn Phe Thr Ala Ala Arg Ala Ser Leu Asn Thr Tyr Arg Leu Tyr Leu
    610                 615                 620
Asn Gly Gly Lys Thr Val Val Ser Ile Arg Pro Leu Ala Asp Gly Gly
625                 630                 635                 640
Met Leu Val Leu Leu Asp Gly Arg Ser His Thr Leu Tyr Trp Arg Glu
                645                 650                 655
Glu Val Gly Thr Leu Arg Ile Gln Val Asp Ala Lys Thr Cys Leu Ile
            660                 665                 670
Glu Gln Glu Asn Asp Pro Thr Gln Leu Arg Ser Pro Ser Pro Gly Lys
        675                 680                 685
Ile Ile Arg Phe Leu Val Glu Ser Gly Asp His Ile Ser Ser Gly Asp
```

-continued

```
            690                 695                 700
Ile Tyr Ala Glu Val Glu Val Met Lys Met Ile Leu Pro Leu Ile Ala
705                     710                 715                 720
Gln Glu Ser Gly His Val Gln Phe Val Lys Gln Ala Gly Val Thr Val
                725                 730                 735
Asp Pro Gly Ala Ile Gly Ile Leu Ser Leu Asp Asp Pro Thr Arg
                740                 745                 750
Val Lys Lys Ala Lys Pro Phe Glu Gly Leu Leu Pro Val Thr Gly Leu
            755                 760                 765
Pro Asn Leu Pro Gly Asn Arg Pro His Gln Arg Leu Gln Phe Gln Leu
770                 775                 780
Glu Ser Ile Tyr Ser Val Leu Asp Gly Tyr Glu Ser Asp Ser Thr Ala
785                 790                 795                 800
Thr Ile Leu Arg Ser Phe Ser Glu Asn Leu Tyr Asp Pro Asp Leu Ala
                805                 810                 815
Phe Gly Glu Ala Leu Ser Ile Ile Ser Val Leu Ser Gly Arg Met Pro
                820                 825                 830
Ala Asp Leu Glu Glu Ser Ile Arg Glu Val Ile Ser Glu Ala Gln Ser
                835                 840                 845
Lys Pro His Ala Glu Phe Pro Gly Ser Lys Ile Leu Lys Val Val Glu
    850                 855                 860
Arg Tyr Ile Asp Asn Leu Arg Pro Gln Glu Arg Ala Met Val Arg Thr
865                 870                 875                 880
Gln Ile Glu Pro Ile Val Gly Ile Ala Glu Lys Asn Val Gly Gly Pro
                885                 890                 895
Lys Gly Tyr Ala Ser Tyr Val Leu Ala Thr Ile Leu Gln Lys Phe Leu
            900                 905                 910
Ala Val Glu Ala Val Phe Ala Thr Gly Ser Glu Glu Ala Ile Val Leu
                915                 920                 925
Gln Leu Arg Asp Glu Asn Arg Glu Ser Leu Asn Asp Val Leu Gly Leu
            930                 935                 940
Val Leu Ala His Ser Arg Leu Ser Ala Arg Ser Lys Leu Val Leu Ser
945                 950                 955                 960
Val Phe Asp Leu Ile Lys Ser Met Gln Leu Leu Asn Asn Thr Glu Gly
                965                 970                 975
Ser Phe Leu His Lys Thr Met Lys Ala Leu Ala Asp Met Pro Thr Lys
                980                 985                 990
Ala Pro Leu Ala Ser Lys Val Ser Leu Lys Ala Arg Glu Ile Leu Ile
            995                 1000                1005
Ser Cys Ser Leu Pro Ser Tyr Glu Glu Arg Leu Phe Gln Met Glu
    1010                1015                1020
Lys Ile Leu Asn Ser Ser Val Thr Thr Ser Tyr Tyr Gly Glu Thr
    1025                1030                1035
Gly Gly Gly His Arg Asn Pro Ser Val Asp Val Leu Thr Glu Ile
    1040                1045                1050
Ser Asn Ser Arg Phe Thr Val Tyr Asp Val Leu Ser Ser Phe Phe
    1055                1060                1065
Lys His Asp Asp Pro Trp Ile Val Leu Ala Ser Leu Thr Val Tyr
    1070                1075                1080
Val Leu Arg Ala Tyr Arg Glu Tyr Ser Ile Leu Asp Met Gln His
    1085                1090                1095
Glu Gln Gly Gln Asp Gly Ala Ala Gly Val Ile Thr Trp Arg Phe
    1100                1105                1110
```

-continued

```
Lys Leu Asn Gln Pro Ile Ala Glu Ser Ser Thr Pro Arg Val Asp
    1115                1120                1125

Ser Asn Arg Asp Val Tyr Arg Val Gly Ser Leu Ser Asp Leu Thr
    1130                1135                1140

Tyr Lys Ile Lys Gln Ser Gln Thr Glu Pro Leu Arg Ala Gly Val
    1145                1150                1155

Met Thr Ser Phe Asn Asn Leu Lys Glu Val Gln Asp Gly Leu Leu
    1160                1165                1170

Asn Val Leu Ser Phe Phe Pro Ala Tyr His His Gln Asp Phe Thr
    1175                1180                1185

Gln Arg His Gly Gln Asp Ser Ala Met Pro Asn Val Leu Asn Ile
    1190                1195                1200

Ala Ile Arg Ala Phe Glu Glu Lys Asp Asp Met Ser Asp Leu Asp
    1205                1210                1215

Trp Ala Lys Ser Val Glu Ser Leu Val Met Gln Met Ser Ala Glu
    1220                1225                1230

Ile Gln Lys Lys Gly Ile Arg Arg Val Thr Phe Leu Val Cys Arg
    1235                1240                1245

Lys Gly Val Tyr Pro Ser Tyr Phe Thr Phe Arg Gln Glu Gly Ala
    1250                1255                1260

Gln Gly Pro Trp Arg Glu Glu Glu Lys Ile Arg Asn Ile Glu Pro
    1265                1270                1275

Ala Leu Ala Ser Gln Leu Glu Leu Asn Arg Leu Ser Asn Phe Lys
    1280                1285                1290

Val Thr Pro Ile Phe Val Asp Asn Arg Gln Ile His Ile Tyr Lys
    1295                1300                1305

Gly Val Gly Lys Glu Asn Ser Ser Asp Val Arg Phe Phe Ile Arg
    1310                1315                1320

Ala Leu Val Arg Pro Gly Arg Val Gln Gly Ser Met Lys Ala Ala
    1325                1330                1335

Glu Tyr Leu Ile Ser Glu Cys Asp Arg Leu Leu Thr Asp Ile Leu
    1340                1345                1350

Asp Ala Leu Glu Val Val Gly Ala Glu Thr Arg Asn Ala Asp Cys
    1355                1360                1365

Asn His Val Gly Ile Asn Phe Ile Tyr Asn Val Leu Val Asp Phe
    1370                1375                1380

Asp Asp Val Gln Glu Ala Leu Ala Gly Phe Ile Glu Arg His Gly
    1385                1390                1395

Lys Arg Leu Trp Arg Leu Arg Val Thr Ala Ser Glu Ile Arg Met
    1400                1405                1410

Val Leu Glu Asp Asp Glu Gly Asn Val Thr Pro Ile Arg Cys Cys
    1415                1420                1425

Ile Glu Asn Val Ser Gly Phe Val Val Lys Tyr His Ala Tyr Gln
    1430                1435                1440

Glu Val Glu Thr Glu Lys Gly Thr Thr Ile Leu Lys Ser Ile Gly
    1445                1450                1455

Asp Leu Gly Pro Leu His Leu Gln Pro Val Asn His Ala Tyr Gln
    1460                1465                1470

Thr Lys Asn Ser Leu Gln Pro Arg Arg Tyr Gln Ala His Leu Val
    1475                1480                1485

Gly Thr Thr Tyr Val Tyr Asp Tyr Pro Asp Leu Phe Val Gln Ser
    1490                1495                1500
```

```
Leu Arg Lys Val Trp Ala Glu Ala Ala Lys Ile Pro His Leu
1505                1510                1515

Arg Val Pro Ser Glu Pro Leu Thr Ala Thr Glu Leu Val Leu Asp
1520                1525                1530

Glu Asn Asn Glu Leu Gln Val Glu Arg Pro Pro Gly Ser Asn
1535                1540                1545

Ser Cys Gly Met Val Ala Trp Ile Phe Thr Met Leu Thr Pro Glu
1550                1555                1560

Tyr Pro Lys Gly Arg Arg Val Val Ala Ile Ala Asn Asp Ile Thr
1565                1570                1575

Phe Lys Ile Gly Ser Phe Gly Pro Lys Glu Asp Asp Tyr Phe Phe
1580                1585                1590

Lys Ala Thr Glu Ile Ala Lys Lys Leu Gly Leu Pro Arg Ile Tyr
1595                1600                1605

Leu Ser Ala Asn Ser Gly Ala Arg Leu Gly Ile Ala Glu Glu Leu
1610                1615                1620

Leu His Ile Phe Lys Ala Ala Phe Val Asp Pro Ala Lys Pro Ser
1625                1630                1635

Met Gly Ile Lys Tyr Leu Tyr Leu Thr Pro Glu Thr Leu Ser Thr
1640                1645                1650

Leu Ala Lys Lys Gly Ser Ser Val Thr Thr Glu Glu Ile Glu Asp
1655                1660                1665

Asp Gly Glu Arg Arg His Lys Ile Thr Ala Ile Ile Gly Leu Ala
1670                1675                1680

Glu Gly Leu Gly Val Glu Ser Leu Arg Gly Ser Gly Leu Ile Ala
1685                1690                1695

Gly Ala Thr Thr Arg Ala Tyr Glu Glu Gly Ile Phe Thr Ile Ser
1700                1705                1710

Leu Val Thr Ala Arg Ser Val Gly Ile Gly Ala Tyr Leu Val Arg
1715                1720                1725

Leu Gly Gln Arg Ala Ile Gln Val Glu Gly Asn Pro Met Ile Leu
1730                1735                1740

Thr Gly Ala Gln Ser Leu Asn Lys Val Leu Gly Arg Glu Val Tyr
1745                1750                1755

Thr Ser Asn Leu Gln Leu Gly Gly Thr Gln Ile Met Ala Arg Asn
1760                1765                1770

Gly Thr Thr His Leu Val Ala Glu Ser Asp Leu Asp Gly Ala Leu
1775                1780                1785

Lys Val Ile Gln Trp Leu Ser Tyr Val Pro Glu Arg Lys Gly Lys
1790                1795                1800

Ala Ile Pro Ile Trp Pro Ser Glu Asp Pro Trp Asp Arg Thr Val
1805                1810                1815

Thr Tyr Glu Pro Pro Arg Gly Pro Tyr Asp Pro Arg Trp Leu Leu
1820                1825                1830

Glu Gly Lys Pro Asp Glu Gly Leu Thr Gly Leu Phe Asp Lys Gly
1835                1840                1845

Ser Phe Met Glu Thr Leu Gly Asp Trp Ala Lys Thr Ile Val Thr
1850                1855                1860

Gly Arg Ala Arg Leu Gly Gly Ile Pro Met Gly Val Ile Ala Val
1865                1870                1875

Glu Thr Arg Thr Thr Glu Lys Ile Ile Ala Ala Asp Pro Ala Asn
1880                1885                1890

Pro Ala Ala Phe Glu Gln Lys Ile Met Glu Ala Gly Gln Val Trp
```

-continued

|  | 1895 |  |  | 1900 |  |  |  | 1905 |  |  |
|---|---|---|---|---|---|---|---|---|---|---|

Asn Pro Asn Ala Ala Tyr Lys Thr Ala Gln Ser Ile Phe Asp Ile
    1910                1915                    1920

Asn Lys Glu Gly Leu Pro Leu Met Ile Leu Ala Asn Ile Arg Gly
    1925                1930                    1935

Phe Ser Gly Gly Gln Gly Asp Met Phe Asp Ala Ile Leu Lys Gln
    1940                1945                    1950

Gly Ser Lys Ile Val Asp Gly Leu Ser Asn Phe Lys Gln Pro Val
    1955                1960                    1965

Phe Val Tyr Val Val Pro Asn Gly Glu Leu Arg Gly Gly Ala Trp
    1970                1975                    1980

Val Val Leu Asp Pro Thr Ile Asn Leu Ala Lys Met Glu Met Tyr
    1985                1990                    1995

Ala Asp Glu Thr Ala Arg Gly Gly Ile Leu Glu Pro Glu Gly Ile
    2000                2005                    2010

Val Glu Ile Lys Phe Arg Arg Asp Lys Val Ile Ala Thr Met Glu
    2015                2020                    2025

Arg Leu Asp Glu Thr Tyr Ala Ser Leu Lys Ala Ala Ser Asn Asp
    2030                2035                    2040

Ser Thr Lys Ser Ala Glu Glu Arg Ala Lys Ser Ala Glu Leu Leu
    2045                2050                    2055

Lys Ala Arg Glu Thr Leu Leu Gln Pro Thr Tyr Leu Gln Ile Ala
    2060                2065                    2070

His Leu Tyr Ala Asp Leu His Asp Arg Val Gly Arg Met Glu Ala
    2075                2080                    2085

Lys Gly Cys Ala Lys Arg Ala Val Trp Ala Glu Ala Arg Arg Phe
    2090                2095                    2100

Phe Tyr Trp Arg Leu Arg Arg Leu Asn Asp Glu His Ile Leu
    2105                2110                    2115

Ser Lys Phe Ala Ala Ala Asn Pro Asp Leu Thr Leu Glu Glu Arg
    2120                2125                    2130

Gln Asn Ile Leu Asp Ser Val Val Gln Thr Asp Leu Thr Asp Asp
    2135                2140                    2145

Arg Ala Thr Ala Glu Trp Ile Glu Gln Ser Ala Glu Glu Ile Ala
    2150                2155                    2160

Ala Ala Val Ala Glu Val Arg Ser Thr Tyr Val Ser Asn Lys Ile
    2165                2170                    2175

Ile Ser Phe Ala Glu Thr Glu Arg Ala Gly Ala Leu Gln Gly Leu
    2180                2185                    2190

Val Ala Val Leu Ser Thr Leu Asn Ala Glu Asp Lys Lys Ala Leu
    2195                2200                    2205

Val Ser Ser Leu Gly Leu
    2210

```
<210> SEQ ID NO 4
<211> LENGTH: 26
<212> TYPE: DNA
<213> ORGANISM: Artificial Sequence
<220> FEATURE:
<223> OTHER INFORMATION: primer acc9
<220> FEATURE:
<221> NAME/KEY: misc_feature
<222> LOCATION: (6)..(6)
<223> OTHER INFORMATION: n is a, c, g or t
<220> FEATURE:
<221> NAME/KEY: misc_feature
<222> LOCATION: (9)..(9)
```

<223> OTHER INFORMATION: n is a, c, g or t
<220> FEATURE:
<221> NAME/KEY: misc_feature
<222> LOCATION: (15)..(15)
<223> OTHER INFORMATION: n is a, c, g or t
<220> FEATURE:
<221> NAME/KEY: misc_feature
<222> LOCATION: (18)..(18)
<223> OTHER INFORMATION: n is a, c, g or t
<220> FEATURE:
<221> NAME/KEY: misc_feature
<222> LOCATION: (21)..(21)
<223> OTHER INFORMATION: n is a, c, g or t
<220> FEATURE:
<221> NAME/KEY: misc_feature
<222> LOCATION: (24)..(24)
<223> OTHER INFORMATION: n is a, c, g or t

<400> SEQUENCE: 4
athggngcnt ayytngynmg nytngg                                    26

<210> SEQ ID NO 5
<211> LENGTH: 25
<212> TYPE: DNA
<213> ORGANISM: Artificial Sequence
<220> FEATURE:
<223> OTHER INFORMATION: primer acc13
<220> FEATURE:
<221> NAME/KEY: misc_feature
<222> LOCATION: (3)..(3)
<223> OTHER INFORMATION: n is a, c, g or t
<220> FEATURE:
<221> NAME/KEY: misc_feature
<222> LOCATION: (6)..(6)
<223> OTHER INFORMATION: n is a, c, g or t
<220> FEATURE:
<221> NAME/KEY: misc_feature
<222> LOCATION: (12)..(12)
<223> OTHER INFORMATION: n is a, c, g or t
<220> FEATURE:
<221> NAME/KEY: misc_feature
<222> LOCATION: (15)..(15)
<223> OTHER INFORMATION: n is a, c, g or t
<220> FEATURE:
<221> NAME/KEY: misc_feature
<222> LOCATION: (18)..(18)
<223> OTHER INFORMATION: n is a, c, g or t
<220> FEATURE:
<221> NAME/KEY: misc_feature
<222> LOCATION: (21)..(21)
<223> OTHER INFORMATION: n is a, c, g or t
<220> FEATURE:
<221> NAME/KEY: misc_feature
<222> LOCATION: (24)..(24)
<223> OTHER INFORMATION: n is a, c, g or t

<400> SEQUENCE: 5
acnacnaccc angcnccncc nckna                                     25

<210> SEQ ID NO 6
<211> LENGTH: 26
<212> TYPE: DNA
<213> ORGANISM: Artificial Sequence
<220> FEATURE:
<223> OTHER INFORMATION: primer acc17

<400> SEQUENCE: 6
ttaccctcgt cgtcctcaag aaccat                                    26

<210> SEQ ID NO 7
<211> LENGTH: 26
<212> TYPE: DNA
<213> ORGANISM: Artificial Sequence -continued

```
<220> FEATURE:
<223> OTHER INFORMATION: primer acc18

<400> SEQUENCE: 7
tggatcctac tatcaacctg ccaaga                                    26

<210> SEQ ID NO 8
<211> LENGTH: 26
<212> TYPE: DNA
<213> ORGANISM: Artificial Sequence
<220> FEATURE:
<223> OTHER INFORMATION: primer acc26

<400> SEQUENCE: 8
gtgaacactg tcttgagagt gtcctt                                    26

<210> SEQ ID NO 9
<211> LENGTH: 20
<212> TYPE: DNA
<213> ORGANISM: Artificial Sequence
<220> FEATURE:
<223> OTHER INFORMATION: primer acc43

<400> SEQUENCE: 9
ccgctgctca gcttcagatt                                           20

<210> SEQ ID NO 10
<211> LENGTH: 19
<212> TYPE: DNA
<213> ORGANISM: Artificial Sequence
<220> FEATURE:
<223> OTHER INFORMATION: primer acc44

<400> SEQUENCE: 10
gattagatag ggatctagt                                            19
```